(12) United States Patent
Gilbride

(10) Patent No.: US 10,932,917 B2
(45) Date of Patent: Mar. 2, 2021

(54) IMPLANT BONE ON-GROWTH STRUCTURES AND METHODS

(71) Applicant: Charles Gilbride, Salinas, CA (US)

(72) Inventor: Charles Gilbride, Salinas, CA (US)

(*) Notice: Subject to any disclaimer, the term of this patent is extended or adjusted under 35 U.S.C. 154(b) by 0 days.

(21) Appl. No.: 16/237,596

(22) Filed: Dec. 31, 2018

(65) Prior Publication Data

US 2019/0201212 A1    Jul. 4, 2019

Related U.S. Application Data

(60) Provisional application No. 62/612,366, filed on Dec. 30, 2017.

(51) Int. Cl.
*A61F 2/44* (2006.01)
*A61F 2/28* (2006.01)
*A61F 2/30* (2006.01)

(52) U.S. Cl.
CPC ............ *A61F 2/4455* (2013.01); *A61F 2/28* (2013.01); *A61F 2/30771* (2013.01);
(Continued)

(58) Field of Classification Search
CPC ............... A61F 2/4455; A61F 2/30771; A61F 2002/3092; A61F 2002/30909;
(Continued)

(56) References Cited

U.S. PATENT DOCUMENTS

| 5,609,635 A | * | 3/1997 | Michelson | A61F 2/442 |
| | | | | 623/17.16 |
| 8,012,210 B2 | * | 9/2011 | Lin | A61F 2/441 |
| | | | | 623/17.12 |

(Continued)

FOREIGN PATENT DOCUMENTS

WO    WO-2020053867 A1 *  3/2020   ........... A61F 2/4455

OTHER PUBLICATIONS

Sasso, "Screws, Cages or Both?", SpineUniverse, Vertical Health, LLC, Sep. 18, 2012 (11 pgs).

(Continued)

*Primary Examiner* — Matthew J Lawson
*Assistant Examiner* — Lisa Nguyen
(74) *Attorney, Agent, or Firm* — David Meibos; Maywood IP Law

(57) ABSTRACT

Medical implants disclosed herein may include an interior space and at least one bone on-growth structure within the interior space. The bone on-growth structure may include a root coupled to an interior surface of the implant, or to a mesh insert disposed within the interior space of the implant. The root may extend into the interior space toward another opposing interior surface of the implant. The bone on-growth structure may include a plurality of branches coupled to the root via a plurality of junctions. The plurality of branches may project at a plurality of different angles with respect to the root. The plurality of branches may each terminate within the interior space, or alternatively, one or more branches may contact opposing interior surfaces of the implant. The medical implants may also include one or more channels to enhance bone growth within the interior space.

17 Claims, 13 Drawing Sheets

(52) U.S. Cl.
CPC ............. *A61F 2002/3085* (2013.01); *A61F 2002/3092* (2013.01); *A61F 2002/30593* (2013.01); *A61F 2002/30909* (2013.01); *A61F 2310/00023* (2013.01); *A61F 2310/00029* (2013.01); *A61F 2310/00059* (2013.01); *A61F 2310/00976* (2013.01)

(58) Field of Classification Search
CPC ............ A61F 2002/3479; A61F 2/0077; A61F 2/30767; A61F 2002/30028; A61F 2002/30029; A61F 2002/3093; A61F 2250/0051; A61F 2002/4435
See application file for complete search history.

(56) References Cited

U.S. PATENT DOCUMENTS

| | | | | |
|---|---|---|---|---|
| 8,292,967 | B2* | 10/2012 | Brown | A61B 17/866 623/23.19 |
| 8,889,178 | B2* | 11/2014 | Bagga | A61L 27/56 424/443 |
| 10,661,390 | B2* | 5/2020 | Bandyopadhyay | A61F 2/30942 |
| 2005/0177237 | A1* | 8/2005 | Shappley | A61F 2/28 623/17.11 |
| 2007/0071789 | A1* | 3/2007 | Pantelidis | A61L 31/16 424/423 |
| 2014/0364961 | A1* | 12/2014 | Mikhail | A61F 2/4644 623/23.52 |
| 2018/0296343 | A1* | 10/2018 | Wei | B29C 64/386 |
| 2019/0076266 | A1* | 3/2019 | Trudeau | A61F 2/30965 |

OTHER PUBLICATIONS

Nuvasive, "Nuvasive Launches 3D-printed Porous Titanium Implant Modulus XLIF", SpinalNews International, Oct. 20, 2017 (2 pgs).
Trahan, "Anterior Lateral Graft Insertion During an ALIF Procedure Using SPIRA Open Matrix Spacer", SPINE, vol. 43, 1-3 pgs, Wolters Kluwer Health, Inc. Jul. 11, 2018.
4WEB Medical, Products, Spine (accessed https://4webmedical.com/products/) Dec. 4, 2019.

* cited by examiner

IMPLANT BONE ON-GROWTH STRUCTURES AND METHODS

CROSS-REFERENCE TO RELATED APPLICATIONS

The present application claims the priority benefit of U.S. Provisional Patent Application Ser. No. 62/612,366 entitled "Interbody Fusion Systems and Methods," filed on Dec. 30, 2017. The foregoing application is incorporated by reference as though set forth herein in its entirety.

TECHNICAL FIELD

The present disclosure relates to medical device implants. More specifically, the present disclosure relates to medical device implants utilizing bone on-growth structures to improve bone in-growth within the medical device implants.

BACKGROUND

Medical device implants may be used in a variety of surgical procedures where bone in-growth within the medical device implant may be desirable. For example, a spinal fusion surgical procedure may include insertion of a spinal fusion cage between a superior vertebra and an inferior vertebra in order to fuse a vertebral joint formed between the superior vertebra and the inferior vertebra. Often times, the ultimate strength of the spinal fusion depends on bone in-growth that occurs within the spinal fusion cage over time, after the spinal fusion cage has been implanted into the vertebral joint of the patient.

Accordingly, it would be desirable to provide improved medical device implants that utilize bone on-growth structures disposed within the medical device implants in order to facilitate bone in-growth therein.

SUMMARY

In some embodiments, an implant may include a superior end, an inferior end, and at least one side wall intermediate to, and coupled with, the superior end and the inferior end of the implant defining an interior space of the implant. The implant may also include a first bone on-growth structure extending within the interior space of the implant. The first bone on-growth structure may include a first root coupled to one of the superior end, the inferior end, and the at least one side wall of the implant. The first root may extend into the interior space of the implant toward another one of the superior end, the inferior end, and the at least one side wall of the implant. The first bone on-growth structure may also include a first plurality of branches coupled to the first root at a first plurality of junctions. The first plurality of branches may project at a first plurality of different angles with respect to the first root.

In other embodiments, an implant may include a fusion cage having a fusion cage superior end, a fusion cage inferior end, and at least one fusion cage side wall intermediate the fusion cage superior end and the fusion cage inferior end defining an interior space of the fusion cage. At least one of the fusion cage superior end and the fusion cage inferior end may be removably couplable from the at least one fusion cage side wall. The implant may also include a mesh insert that is removably disposable within the interior space of the fusion cage. The mesh insert may include a mesh insert superior end, a mesh insert inferior end, and at least one mesh insert side wall intermediate to, and coupled with, the mesh insert superior end and the mesh insert inferior end to define an interior space of the mesh insert. The mesh insert may also include a first bone on-growth structure extending within the interior space of the mesh insert. The first bone on-growth structure may include a first root coupled to one of the mesh insert superior end, the mesh insert inferior end, and the at least one mesh insert side wall. The first root may extend into the interior space of the mesh insert toward another one of the mesh insert superior end, the mesh insert inferior end, and the at least one mesh insert side wall. The first bone on-growth structure may also include a first plurality of branches coupled to the first root at a first plurality of junctions. The first plurality of branches may project at a first plurality of different angles with respect to the first root.

In yet other embodiments, a method of facilitating bone on-growth within an implantable medical device include providing a medical device. The medical device may include a superior end, an inferior end, and at least one side wall intermediate to, and coupled with, the superior end and the inferior end defining an interior space of the medical device. The medical device may also include a first bone on-growth structure extending within the interior space of the medical device. The first bone on-growth structure may include a first root coupled to one of the superior end, the inferior end, and the at least one side wall of the medical device. The first root may extend into the interior space of the medical device toward another one of the superior end, the inferior end, and the at least one side wall of the medical device. The first bone on-growth structure may also include a first plurality of branches coupled to the first root at a first plurality of junctions. The first plurality of branches may project at a first plurality of different angles with respect to the first root. The method may also include implanting the medical device within a patient to facilitate bone on-growth along the first bone on-growth structure within the medical device.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

Figure 1:
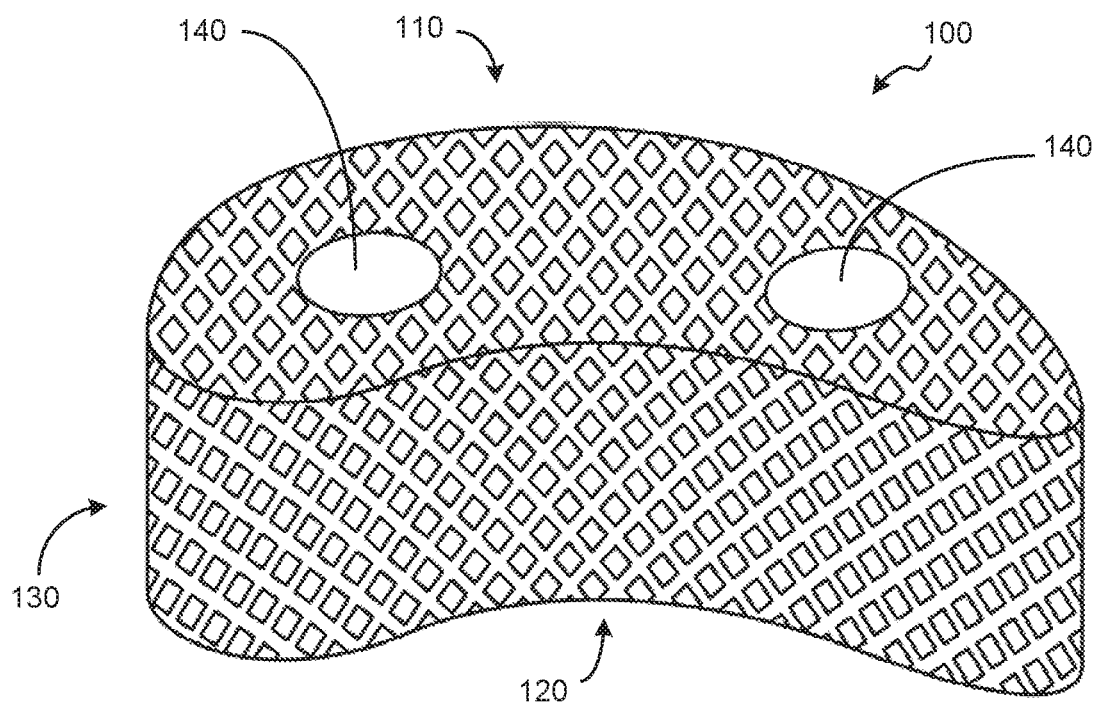
FIG. 1 is a top perspective view of an implant, according to an embodiment of the disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the figures, is not intended to limit the scope of the present disclosure, as claimed in this or any other application claiming priority to this application, but is merely representative of exemplary embodiments of the present disclosure.

For simplicity, the example implants described herein are illustrated in the context of spinal fusion spacers. However, it will be understood that the bone on-growth structures of the present disclosure may be utilized in other orthopedic procedures and applications that involve bone or other tissue on-growth. Moreover, although the various implant shapes disclosed herein are commonly used in spinal fusion applications, it will be understood that the bone on-growth structures disclosed herein may be utilized with implants of any size, shape, or application. For example, the implants described herein may have planar and/or cylindrical shapes as shown, or may have more irregular shapes, for example, defined by the interconnection of bone on-growth structures. Implants including bone on-growth structures described herein may be used in connection with procedures involving fusion of other joints, bone replacement, bone fracture repair, and/or the like. In some embodiments, these implants may be custom-manufactured to have the shape needed for the particular procedure. Those of skill in the art will recognize that may other variations, besides those specifically set forth herein, may be utilized. For example, where an implant is utilized to replace all or part of a bone, the implant may be manufactured to have the shape of the bone, or portion of bone, that is to be replaced.

Various manufacturing methods for the implant described herein are envisioned. According to some methods, implants may be made through additive manufacturing methods such as 3D printing. In some embodiments, the members that make up the implant may be grown or deposited chemically, mechanically, or otherwise. Various biocompatible materials are also envisioned, including but not limited to Titanium, Cobalt Chromium, metal alloys, textured surfaces, nano-textured surfaces, etc. In some embodiments, biocompatible polymers such as PEEK, ultra-high molecular weight polyethylene (UHMWPE), and the like, may be used. In yet other embodiments, biocompatible ceramics may be used. In still other embodiments, the implant may be a mixture of metal, polymer, and/or ceramic materials. In still further embodiments, biologics and/or bioactive agents may be utilized to coat all or part of the implants disclosed herein to enhances healing, bone-ingrowth, biocompatibility, and/or the like including, but not limited to: hydroxyapatite, demineralized bone matrix ("DBM"), bone morphogenetic proteins ("BMP"), stem cells, and the like.

The implants disclosed herein may utilize various structures and configurations. For example, the superior ends, inferior ends, and/or side walls of implants disclosed herein may, in some embodiments, consist of solid walls or surfaces. These solid walls or surfaces may optionally be formed as a single piece including the internal bone on-growth structures within such implants. In the alternative, the superior ends, inferior ends, and/or side walls of implants disclosed herein may, in some embodiments, include walls or surfaces that are porous and/or flexible. For example, in some embodiments a mesh structure may be utilized including bone on-growth structures that couple to surfaces of the mesh structure and extend within an interior space of the mesh structure. Such a porous structure may facilitate bone in-growth after the implant has been implanted adjacent to bony tissue within a patient, such as between vertebral bodies. In some embodiments, the superior ends and/or the inferior ends may be intentionally ridged, spiked, or otherwise roughened to define bone engagement surfaces that keep the device in place between vertebral bodies. Furthermore, although implants depicted in the Figures of the present disclosure illustrate the superior ends and the inferior ends of the implants oriented generally parallel to each other, in some embodiments, they may be non-parallel, for example, to maintain the natural lordosis and/or kyphosis of a vertebral level that is to be stabilized. Such implants may be used in the lumbar, thoracic, and/or cervical spine. In some embodiments, the superior end and the inferior end of the implant may be movable relative to each other to permit the implant to expand between the vertebrae, to permit adjustment of an angle between the superior end and the inferior end of the implant, and/or the like. For example, a hinge, telescoping mechanism, or other mechanical linkage may be used to provide such relative motion.

The walls or surfaces of implants disclosed herein may optionally include one or more channels, passageways, or apertures formed in the solid walls or surfaces of the implants. These channels may receive one or more materials that promote bone in-growth within these channels (e.g., bone graft material, etc.). Furthermore, these channels may, in some embodiments, partially penetrate an implant (e.g., penetrate through one surface of the implant). In other embodiments, these channels may fully penetrate an implant (e.g., a channel may penetrate all the way through both opposing surfaces of an implant). In some embodiments, channels formed through an implant may accommodate various anchoring elements, such as screws, nails, pins, barbed fasteners, and the like, which may secure the implant to bone (e.g., one or both adjoining vertebral bodies).

The bone on-growth structures described herein may include roots and branches. Each bone on-growth structure may include multiple junctions leading from a root to a plurality of branches. Each junction may join two or more branches to each root or parent branch. All junctions may have the same number of branches. Alternatively, some junctions may lead from a root or parent branch to two branches, while others may lead to three branches, four branches, etc. The number of branches in each junction may be random. In some embodiments, the roots and/or branches may all have about the same diameter. In other embodiments, consistent variation in size may be present. For example, the branches from each root or parent branch may be about half the diameter of the root or parent branch. In yet other embodiments, the variation in size between different branches may be inconsistent and/or random. Many variations of bone on-growth structures are envisioned, and will be discussed in more detail below. For example, the roots of bone on-growth structures disclosed herein may originate on the superior end of the implant, the inferior end of the implant, a side wall of the implant, the interior of the implant, the exterior of the implant, and/or any combination thereof. The branches of bone on-growth structures disclosed herein may terminate within an interior space of the implant, exterior to the implant, at the superior end of the implant, at the inferior end of the implant, at a side wall of the implant, and/or any combination thereof.

Figure 2:
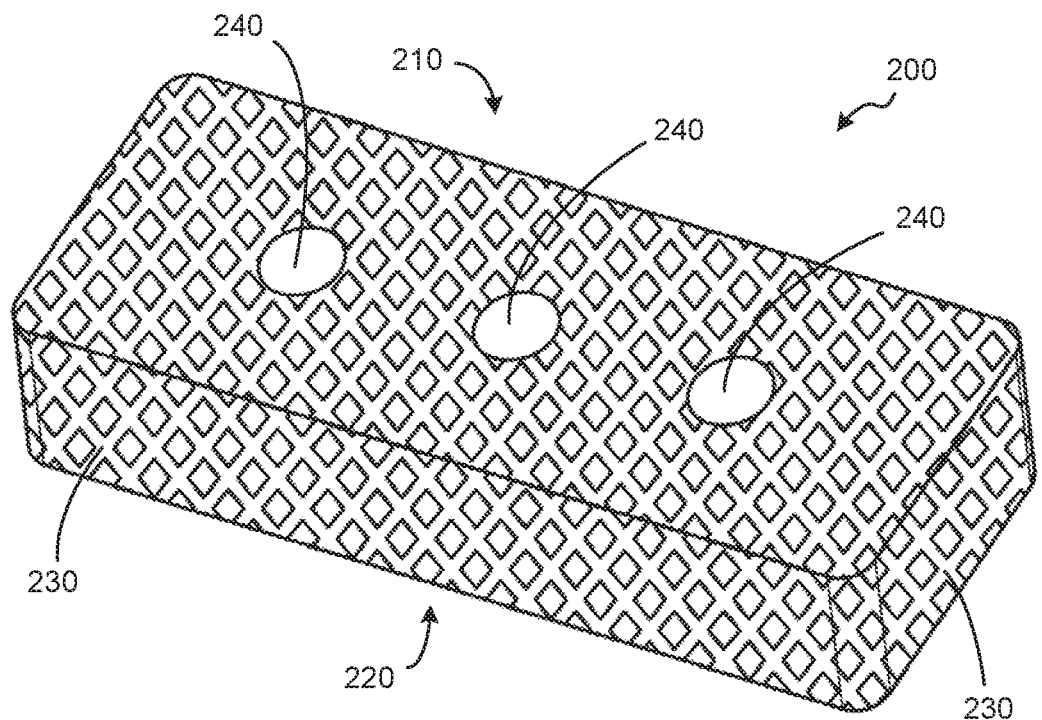
FIG. 2 is a top perspective view of an implant, according to an embodiment of the disclosure.
Figure 3A:
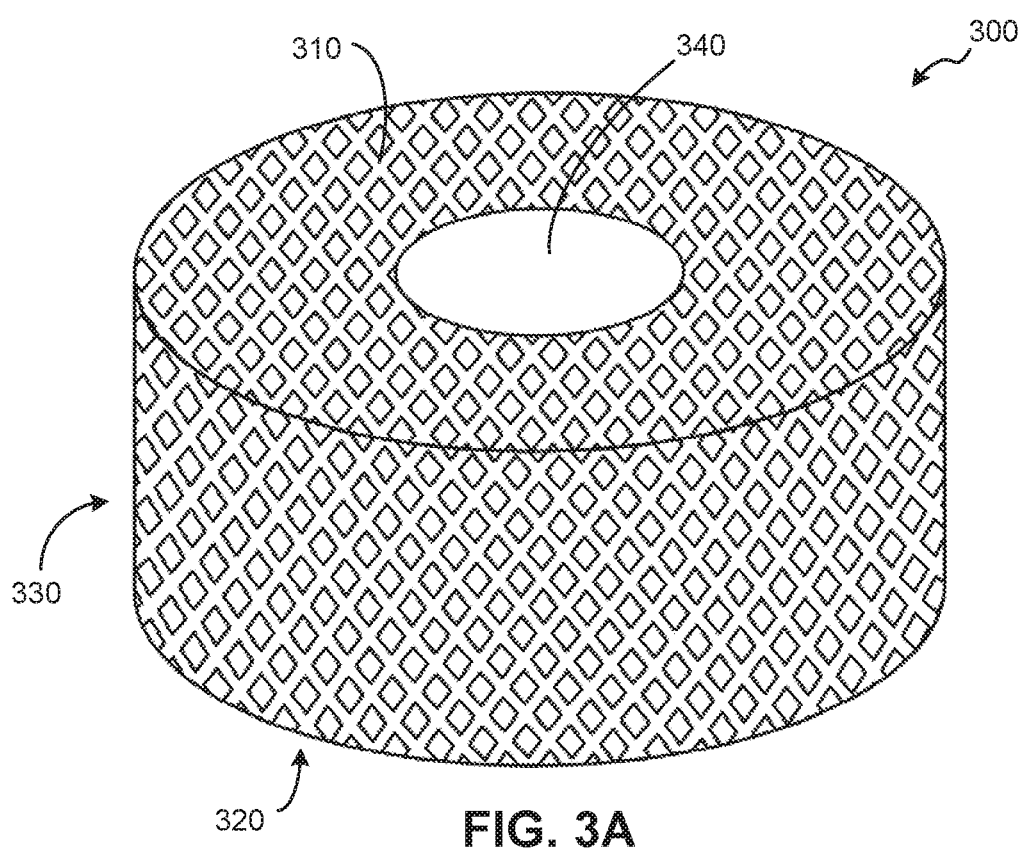
FIG. 3A is a top perspective view of an implant, according to an embodiment of the disclosure.

FIGS. 1-3A illustrate various top perspective views of example implants 100, 200, 300 having different shapes that may be utilized with the bone on-growth structures of the present disclosure. However, as noted above, implants of any shape or size may be utilized with the bone on-growth structures disclosed herein. FIG. 1 is a top perspective view of an implant having a banana shape; FIG. 2 is a top perspective view of an implant having a rectangular shape; and FIG. 3A is a top perspective view of an implant having a cylindrical shape.

The implant shown in FIG. 1 may include a superior end 110, an inferior end 120, and at least one side wall 130 that is intermediate the superior end 110 and the inferior end 120. The side wall 130 may be coupled to both the superior end 110 and the inferior end 120. In the example implant 100 shown in FIG. 1, the side wall 130 comprises a single, continuous wall that encompasses the entire implant 100 intermediate the superior end 110 and the inferior end 120 of the implant 100. An interior space of the implant 100 may be defined by a combination of the superior end 110, the inferior end 120, and the at least one side wall 130, which may together at least partially enclose the interior space of the implant 100. The implant 100 may also include one or more channels 140 (e.g., two channels in this example) that are formed in at least one of the superior end 110, the inferior end 120, and the at least one side wall 130 of the implant.

Likewise, the implant shown in FIG. 2 may include a superior end 210, an inferior end 220, and at least one side wall 230 that is intermediate the superior end 210 and the inferior end 220 of the implant 200. In the example implant 200 shown in FIG. 2, the side wall 230 comprises multiple walls (e.g., four side walls 230 in this example), which together encompass the entire implant 200 intermediate the superior end 210 and the inferior end 220 of the implant 200. The side walls 230 may be coupled to both the superior end 210 and the inferior end 220. An interior space of the implant 200 may likewise be defined by a combination of the superior end 210, the inferior end 220, and the side walls 230, which may together at least partially enclose an interior space of the implant 200. The implant 200 is also shown with one or more channels 240 (e.g., three channels in this example) that are formed in at least one of the superior end 210, the inferior end 220, and the side walls 230.

Figure 3B:
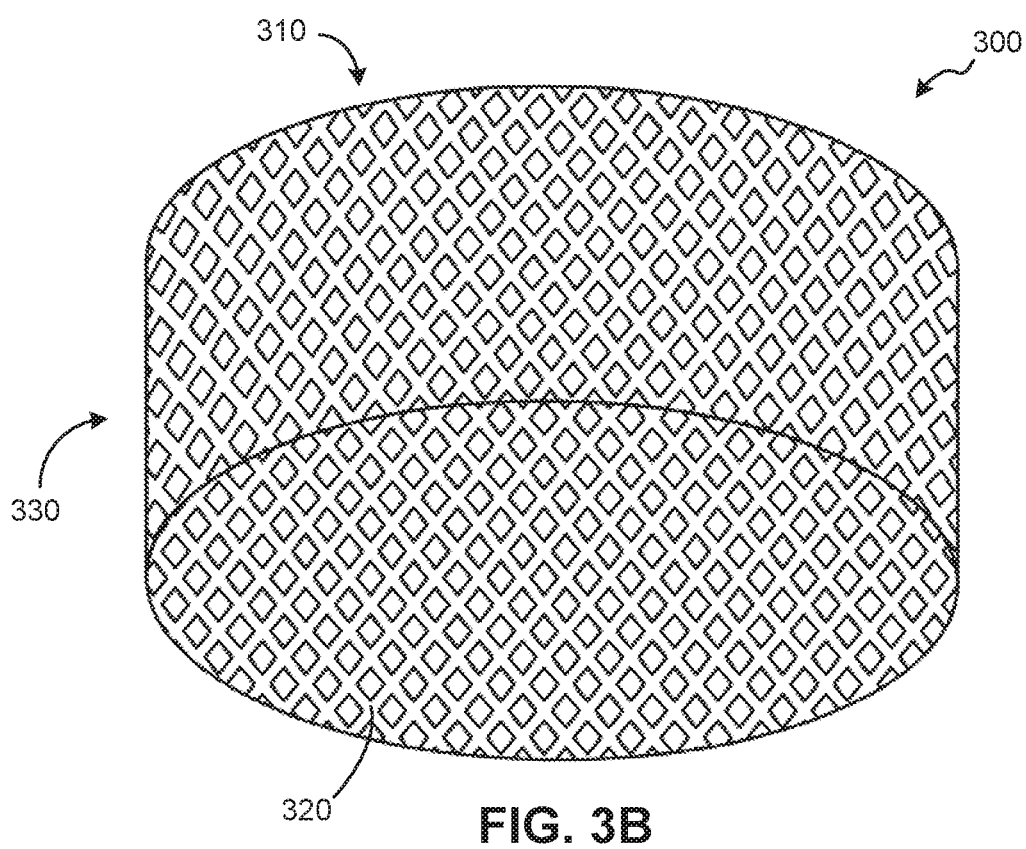
FIG. 3B is a bottom perspective view of the implant of FIG. 3A.
Figure 3C:
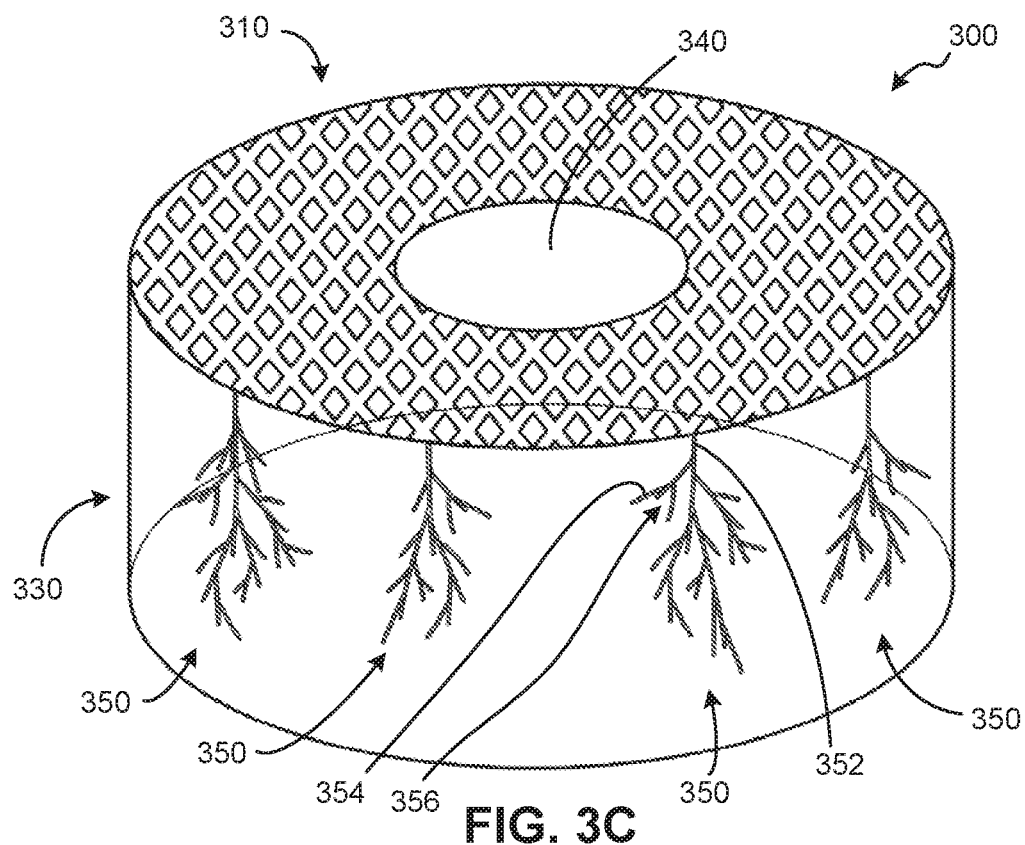
FIG. 3C is a top perspective view of the implant of FIG. 3A illustrating various bone on-growth structures inside the implant.
Figure 3D:
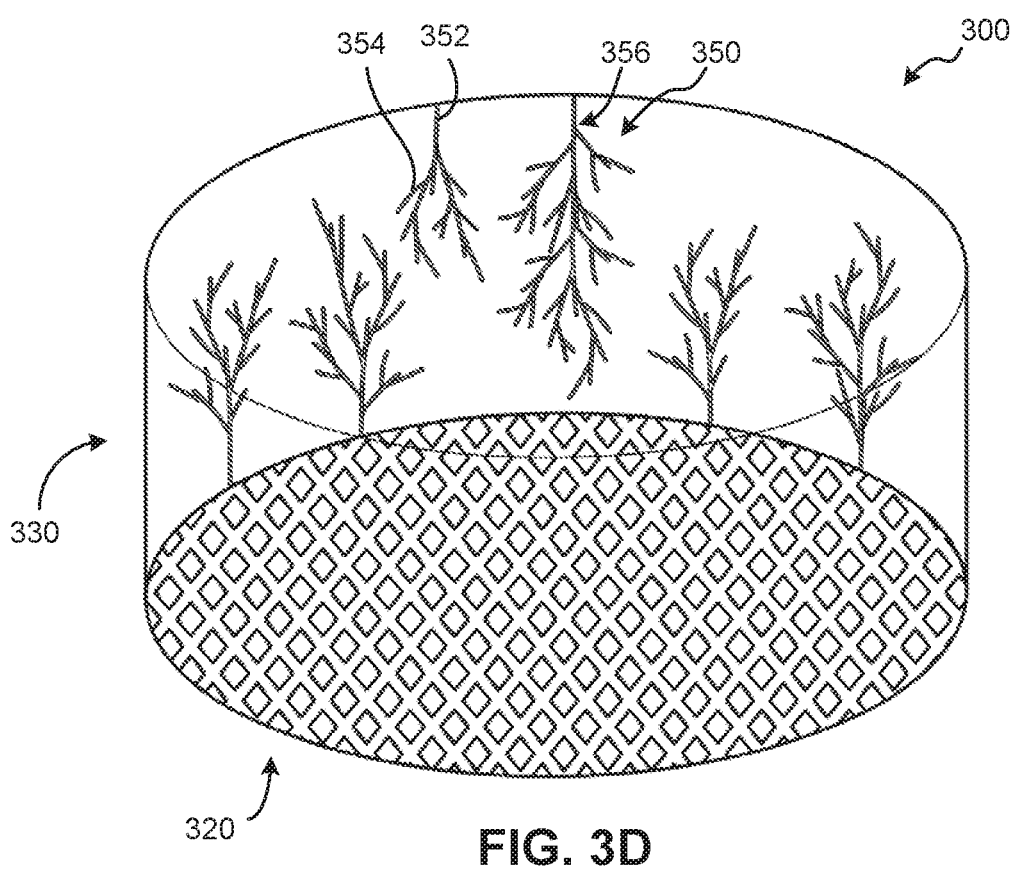
FIG. 3D is a bottom perspective view of the implant of FIG. 3A illustrating various bone on-growth structures inside the implant.

FIGS. 3A-3D illustrate an implant 300 with a cylindrical shape, according to an embodiment of the disclosure. FIG. 3A is a top perspective view of the implant 300; FIG. 3B is a bottom perspective view of the implant 300; FIG. 3C is a top perspective view of the implant 300 with a transparent side wall 330, illustrating the bone on-growth structures 350 inside the implant 300; and FIG. 3D is a bottom perspective view of the implant 300 with a transparent side wall 330 to further illustrate the bone on-growth structures 350 within the implant 300.

The implant shown in FIGS. 3A-3D includes a superior end 310, an inferior end 320, and a side wall 330 intermediate the superior end 310 and the inferior end 320 of the implant 300. The side wall 330 may be coupled to both the superior end 310 and the inferior end 320 of the implant 300. In the example implant 300 shown in FIGS. 3A-3D, the side wall 330 comprises a single, continuous wall that encompasses the entire implant 300 intermediate the superior end 310 and the inferior end 320 of the implant 300. An interior space of the implant 300 is defined by a combination of the superior end 310, the inferior end 320, and the side wall 330, which together enclose the interior space of the implant 300. The implant 300 may also include one or more channels 340 formed in at least one surface of the implant 300 (e.g., in this example one channel 340 is formed in the superior end 310 of the implant 300).

The implant shown in FIGS. 3A-3D includes multiple bone on-growth structures 350 that extend within the interior space of the implant 300. Each bone on-growth structure 350 may include a root 352 that may be coupled to one of the superior end 310, the inferior end 320, and the side wall 330 of the implant 300. The roots 352 may be coupled to any surface of the superior end 310, the inferior end 320, and the side wall 330 of the implant 300, including any interior surface, exterior surface, and/or intermediate surface (e.g., any surface located intermediate an interior surface and an exterior surface) of the superior end 310, the inferior end 320, and the side wall 330 of the implant 300. Each root 352 may extend into the interior space of the implant 300 toward another one of the superior end 310, the inferior end 320, and the side wall 330 of the implant 300. Each bone on-growth structure 350 may further include a plurality of branches 354 coupled to the root 352 via a plurality of junctions 356.

As used herein, the phrase "coupled to" is broadly defined to encompass two or more components (e.g., roots/branches) that are mechanically and/or functionally coupled to each other, even though they may not be in direct contact with each other.

The plurality of branches 354 may each project from a parent branch, or from the root 352, at a plurality of different angles with respect to the root 352 in order to form a particular bone on-growth structure 350. In this manner, each bone on-growth structure 350 may form a scaffold-like structure on which bone tissue (or other tissues) may form to facilitate bone on-growth processes within the implant 300. The implant 300 shown in FIG. 3D includes multiple bone on-growth structures 350 with roots 352 that may be coupled to opposing ends of the implant 300 (e.g., the superior end 310 and the inferior end 320). However, different bone on-growth structure embodiments and configurations will be discussed in more detail below with respect to FIGS. 6-13.

Figure 4:
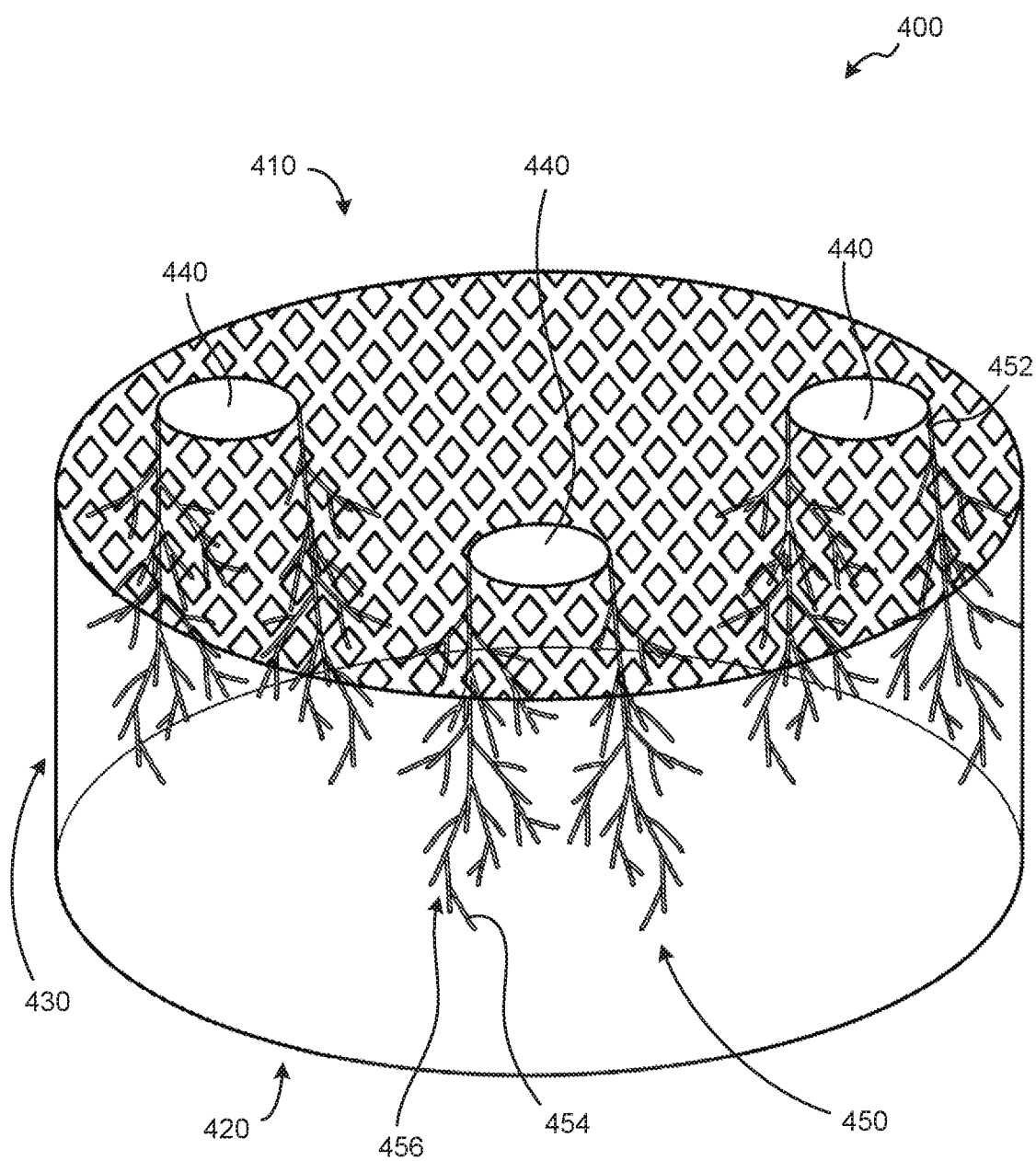
FIG. 4 is a top perspective view of an implant illustrating various bone on-growth structures, according to an embodiment of the disclosure.

FIG. 4 illustrates another implant 400 with a cylindrical shape, according to an embodiment of the disclosure. The implant 400 shown in FIG. 4 includes a superior end 410, an inferior end 420, and a side wall 430 (shown as transparent) intermediate the superior end 410 and the inferior end 420 of the implant 400. The side wall 430 is coupled to both the superior end 410 and the inferior end 420 of the implant 400. The side wall 430 comprises a single, continuous wall that encompasses the entire implant 400 intermediate the superior end 410 and the inferior end 420 of the implant 400. An interior space of the implant 400 is similarly defined by a combination of the superior end 410, the inferior end 420, and the side wall 430, which together enclose the interior space of the implant 400. The implant 400 also includes three channels 440 formed in the superior end 410 of the implant 400, but which do not penetrate all the way through the opposing end (e.g., the inferior end 420) of the implant 400.

The implant 400 also includes multiple bone on-growth structures 450 with roots 452, co branches 454, and junctions 456, which may extend within the interior space of the implant 400. However, the roots 452 of the bone on-growth structures 450 may be coupled at or near the edges of the channels 440 that are formed in the superior end 410 of the implant 400. The bone on-growth structures 450 may extend into the interior space of the implant 400 toward an opposing end (e.g., the inferior end 420) of the implant 400. In this example, each of the branches 454 of the bone on-growth structures 450 terminate within the interior space of the implant 400, such that they do not sufficiently extend within the interior space of the implant 400 to contact an opposing end of the implant 400.

Figure 5:
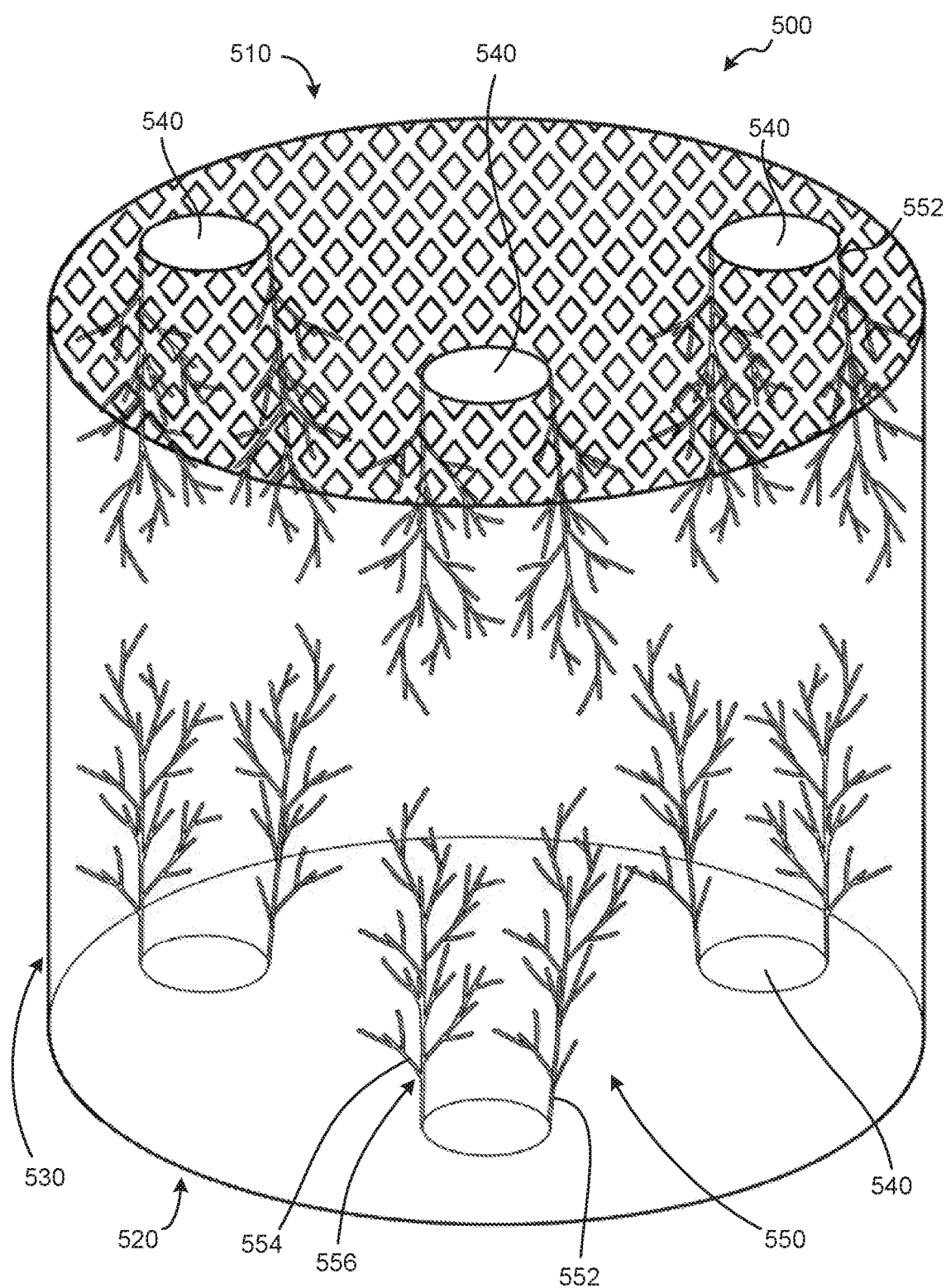
FIG. 5 is a top perspective view of an implant illustrating various bone on-growth structures, according to an embodiment of the disclosure.

FIG. 5 illustrates another implant 500 with a cylindrical shape, according to an embodiment of the disclosure. The implant 500 shown in FIG. 5 includes a superior end 510, an inferior end 520, and a side wall 530 (shown as transparent) intermediate the superior end 510 and the inferior end 520 of the implant 500. The side wall 530 is coupled to both the superior end 510 and the inferior end 520 of the implant 500. The side wall 530 comprises a single, continuous wall that encompasses the entire implant 500 intermediate the superior end 510 and the inferior end 520 of the implant 500. An interior space of the implant 500 is similarly defined by a combination of the superior end 510, the inferior end 520, and the side wall 530, which together enclose the interior space of the implant 500. The implant 500 further includes three channels 540 which are formed all the way through opposing ends of the implant 500 (e.g., through the superior end 510 and the inferior end 520 of the implant 500).

The implant 500 also includes multiple bone on-growth structures 550 with roots 552, branches 554, and junctions 556, which extend into the interior space of the implant 500. The roots 552 of the bone on-growth structures 550 may be coupled at or near the edges of the channels 540 formed in the superior end 510 and the inferior end 520 of the implant 500. The bone on-growth structures 550 may extend into the interior space of the implant 500 toward an opposing end of the implant 500. In this example, each of the branches 554 of the bone on-growth structures 550 terminate within the interior space of the implant 500, such that they do not sufficiently extend within the interior space of the implant 500 to contact the branches 554 of bone on-growth structures 550 extending in the opposite direction within the implant 500.

FIGS. 6-13 illustrate various side views of implants 600, 700, 800, 900, 1000, 1100, 1200, 1300 that incorporate different bone on-growth structures arranged in different configurations. These different bone on-growth structure configurations are just some non-limiting examples of different arrangements that may be used with the implants discussed herein. It will be understood that other bone on-growth structure configurations are also contemplated. For example some bone on-growth structure configurations may include a bone on-growth structure with one or more branches that extend toward and contact an opposing end of an implant, as well as other branches from the same bone on-growth structure that simultaneously extend toward and contact another end of the implant (e.g., a side wall), etc.

Figure 6:
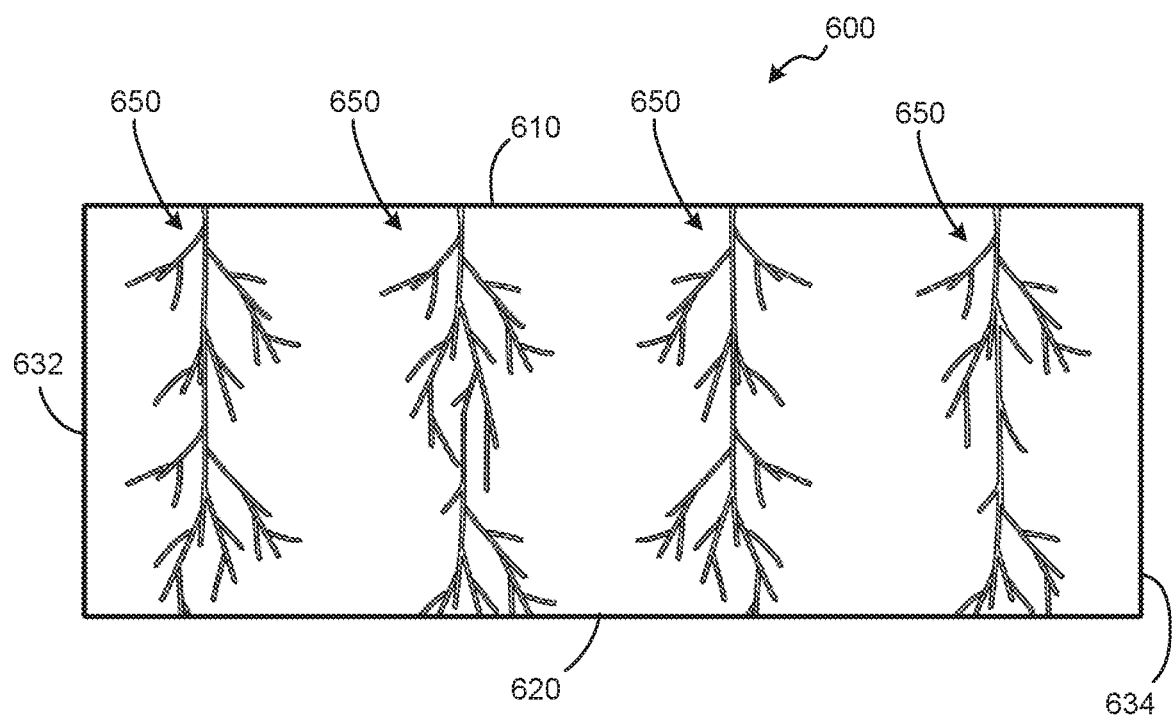
FIG. 6 is a side view of an implant illustrating various bone on-growth structures, according to an embodiment of the disclosure.

FIG. 6 illustrates a side view of an implant 600 having a superior end 610, an inferior end 620, a left side wall 632, a right side wall 634, and multiple bone on-growth structures 650. Each of the bone on-growth structures 650 has a root coupled to the superior end 610 of the implant 600 and at least one branch that sufficiently extends toward an opposing end of the implant 600 (e.g., in this example the inferior end 620 of the implant 600), such that at least one branch contacts the opposing end of the implant 600.

Figure 7:
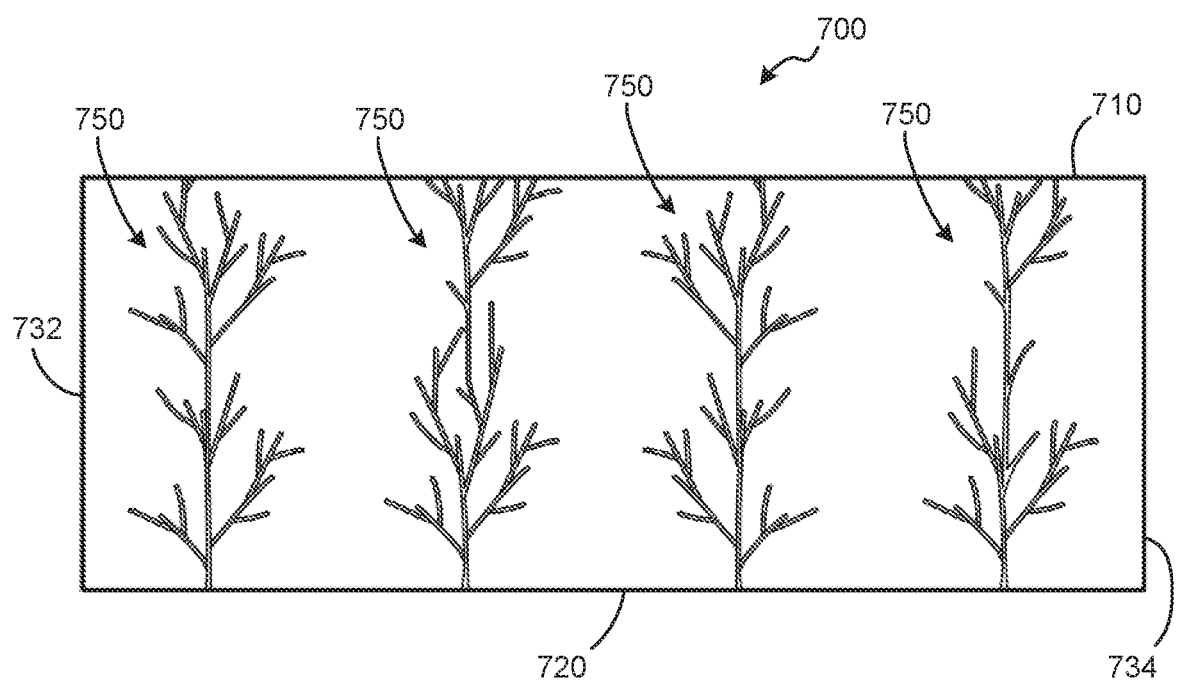
FIG. 7 is a side view of an implant illustrating various bone on-growth structures, according to an embodiment of the disclosure.

FIG. 7 illustrates a side view of an implant 700 having a superior end 710, an inferior end 720, a left side wall 732, a right side wall 734, and multiple bone on-growth structures 750. Each of the bone on-growth structures 750 has a root coupled to the inferior end 720 of the implant 700 and at least one branch that sufficiently extends toward an opposing end of the implant 700 (e.g., in this example the superior end 710 of the implant 700), such that at least one branch contacts the opposing end of the implant 700.

Figure 8:
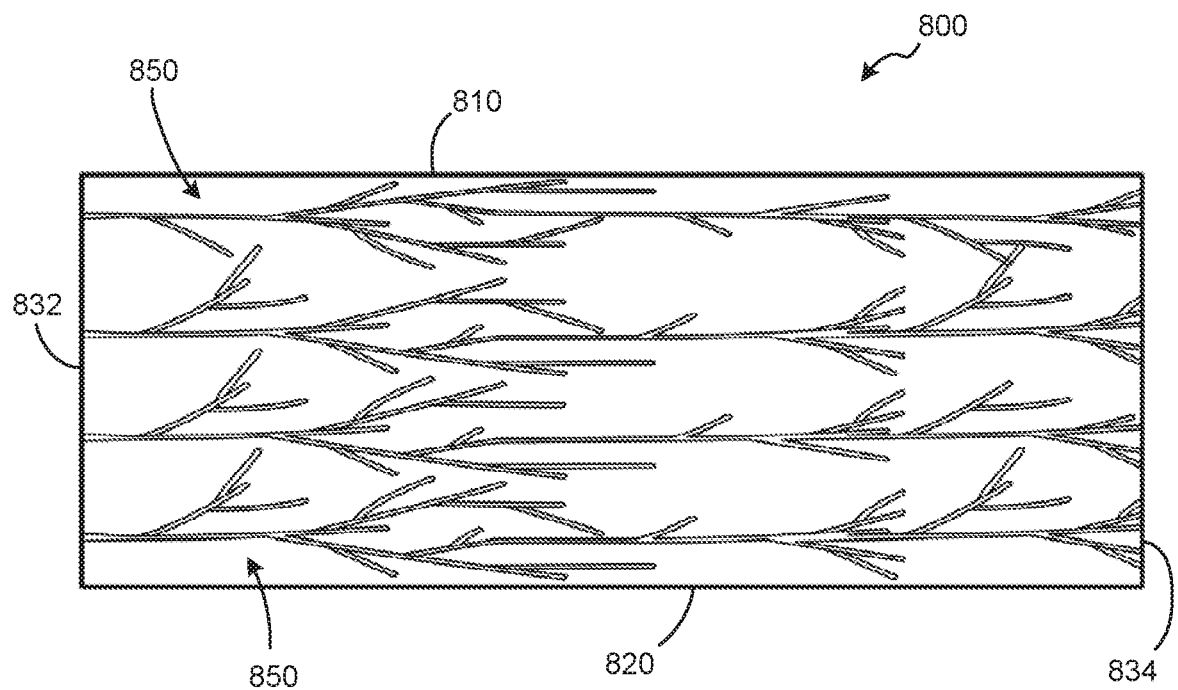
FIG. 8 is a side view of an implant illustrating various bone on-growth structures, according to an embodiment of the disclosure.

FIG. 8 illustrates a side view of an implant 800 having a superior end 810, an inferior end 820, a left side wall 832, a right side wall 834, and multiple bone on-growth structures 850. Each of the bone on-growth structures 850 has a root coupled to the left side wall 832 of the implant 800, and at least one branch that sufficiently extends toward an opposing end of the implant 800 (e.g., in this example the right side wall 834 of the implant 800), such that at least one branch contacts the opposing end of the implant 800.

Figure 9:
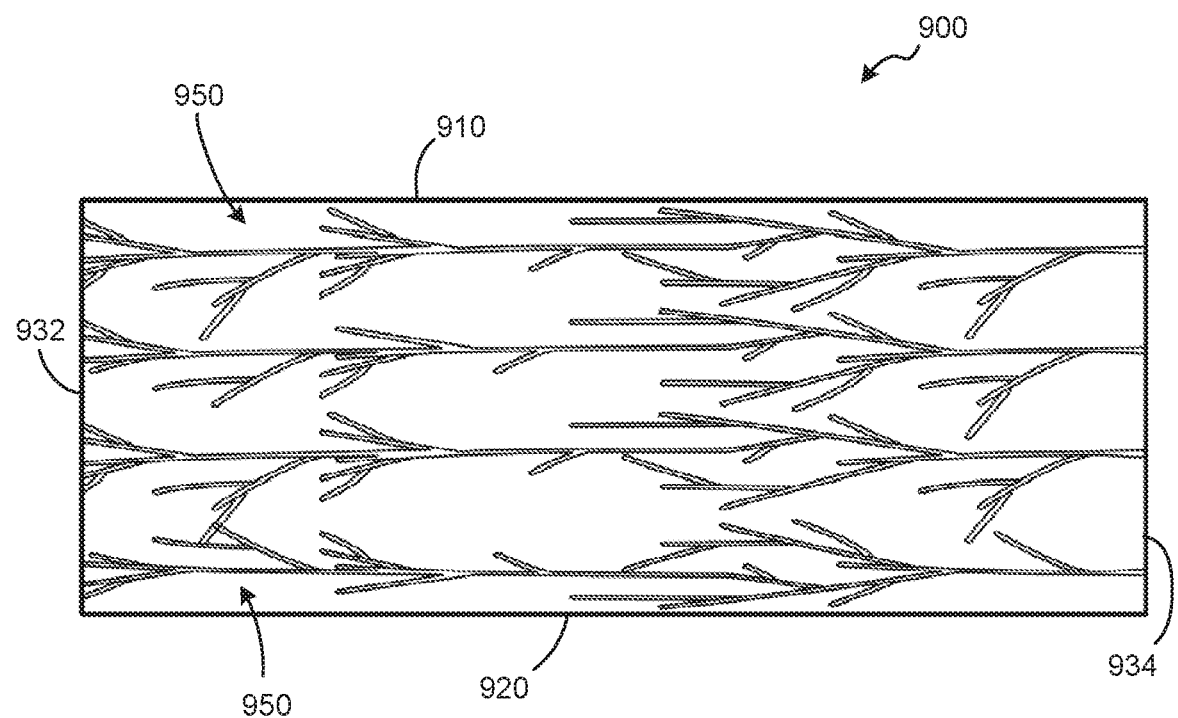
FIG. 9 is a side view of an implant illustrating various bone on-growth structures, according to an embodiment of the disclosure.

FIG. 9 illustrates a side view of an implant 900 having a superior end 910, an inferior end 920, a left side wall 932, a right side wall 934, and multiple bone on-growth structures 950. Each of the bone on-growth structures 950 has a root coupled to the right side wall 934 of the implant 900, and at least one branch that sufficiently extends toward an opposing end of the implant 900 (e.g., in this example the left side wall 932 of the implant 900), such that at least one branch contacts the opposing end of the implant 900.

Figure 10:
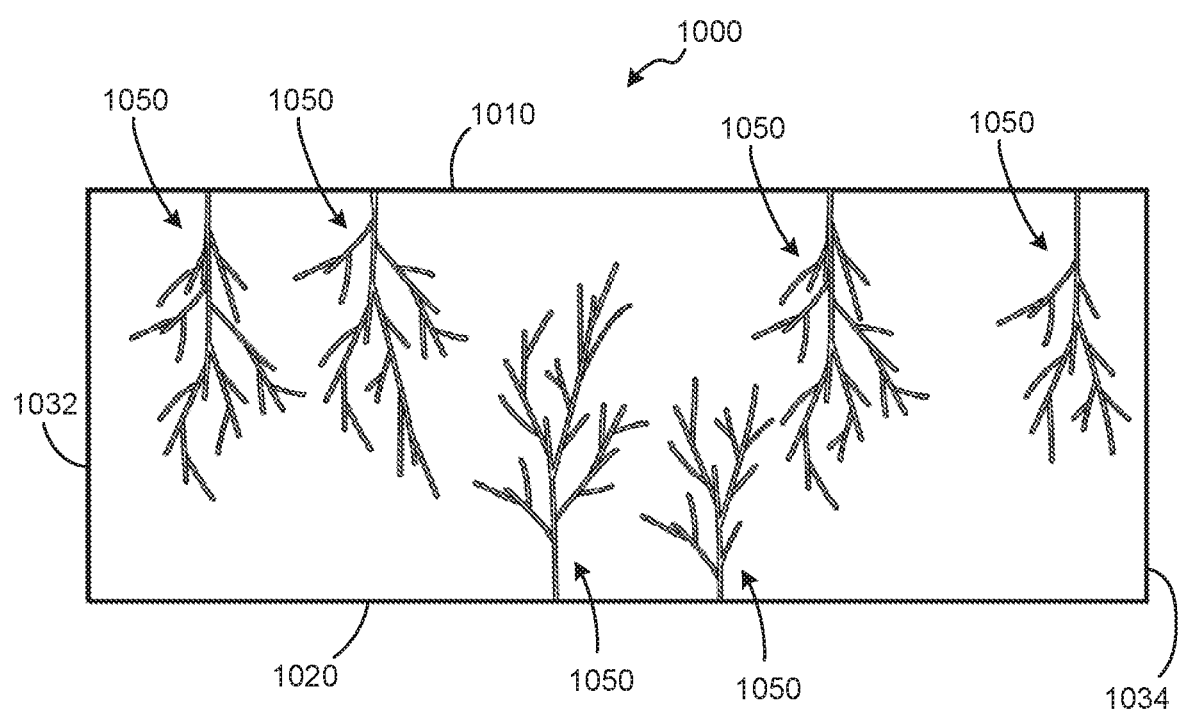
FIG. 10 is a side view of an implant illustrating various bone on-growth structures, according to an embodiment of the disclosure.

FIG. 10 illustrates a side view of an implant 1000 having a superior end 1010, an inferior end 1020, a left side wall 1032, a right side wall 1034, and multiple bone on-growth structures 1050. Some of the bone on-growth structures 1050 have a root coupled to the superior end 1010 of the implant 1000, and other bone on-growth structures 1050 have a root coupled to the inferior end 1020 of the implant 1000. In this example, none of the bone on-growth structures 1050 include a root that is directly aligned opposite another root along the superior and inferior ends 1010, 1020 of the implant 1000. Moreover, in this example, none of the branches of the bone on-growth structures 1050 sufficiently extends toward an opposing end of the implant 1000, such that at least one branch contacts an opposing end of the implant 1000. Rather, each branch of the bone on-growth structures 1050 terminates within the interior space of the implant 1000.

Figure 11:
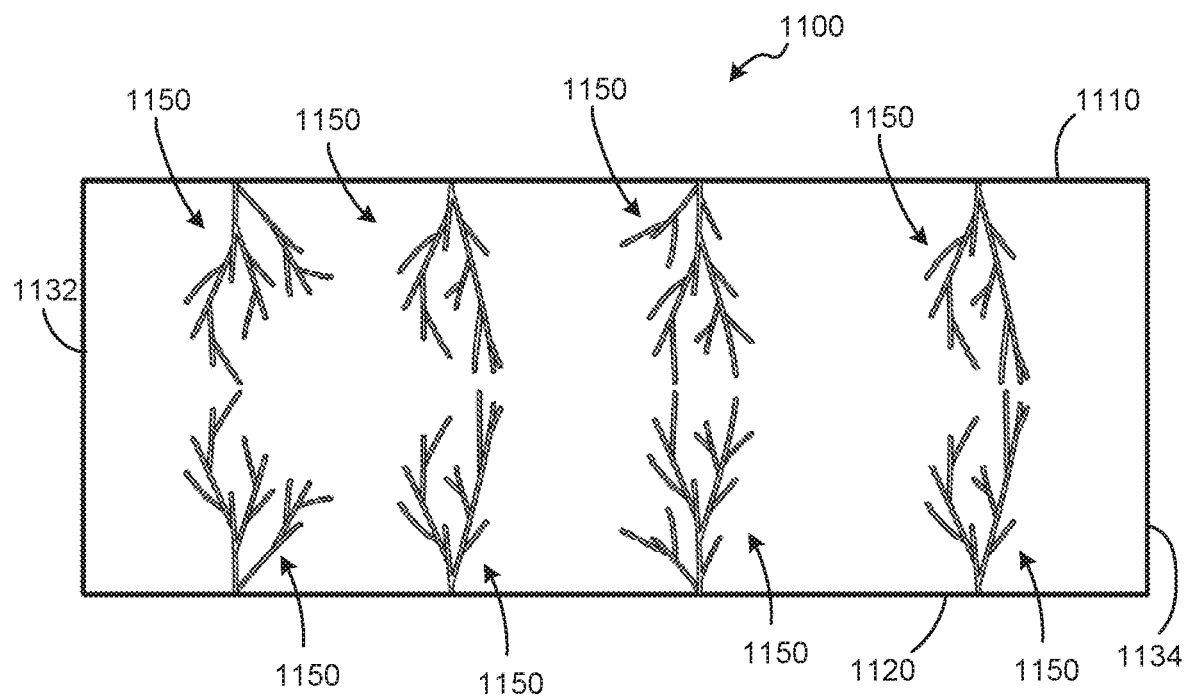
FIG. 11 is a side view of an implant illustrating various bone on-growth structures, according to an embodiment of the disclosure.

FIG. 11 illustrates a side view of an implant 1100 having a superior end 1110, an inferior end 1120, a left side wall 1132, a right side wall 1134, and multiple bone on-growth structures 1150. Some of the bone on-growth structures 1150 have a root coupled to the superior end 1110 of the implant 1100, and other bone on-growth structures 1150 have a root coupled to the inferior end 1120 of the implant 1100. In this example, each of the bone on-growth structures 1150 includes a root that is directly aligned opposite another root along the superior and inferior ends 1110, 1120 of the implant 1100. Moreover, in this example, none of the branches of the bone on-growth structures 1150 sufficiently extends toward an opposing end of the implant 1100, such that at least one branch contacts an opposing end of the implant 1100. Rather, each branch of the bone on-growth structures 1150 terminates within the interior space of the implant 1100.

Figure 12:
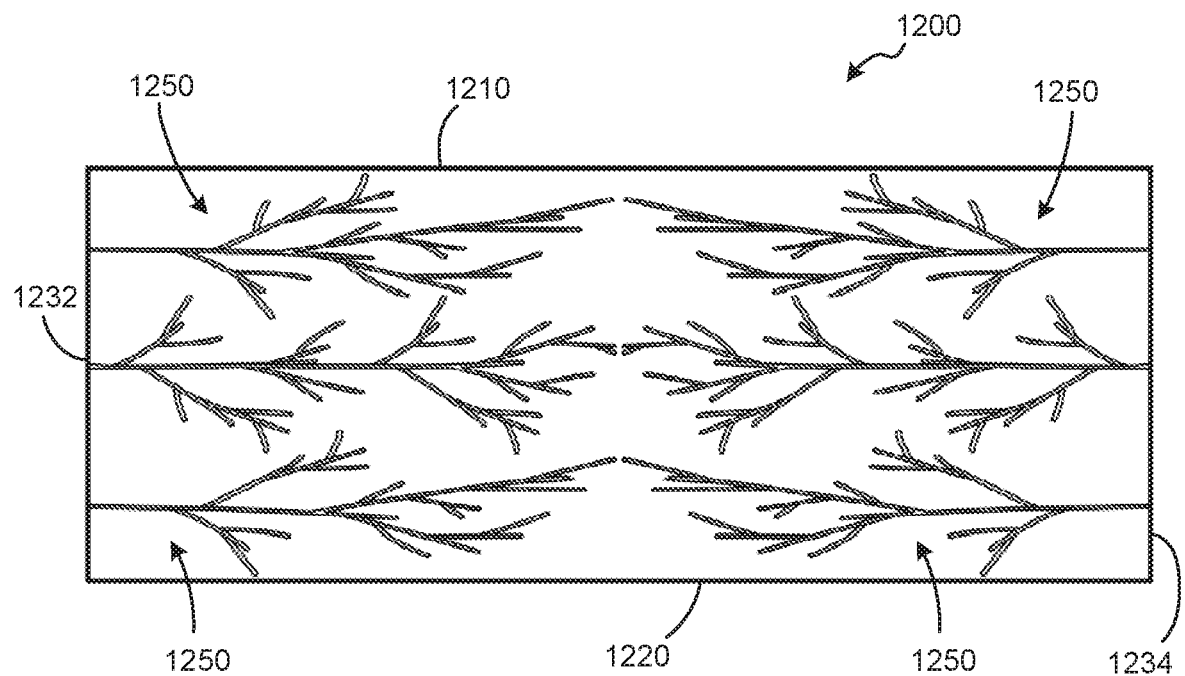
FIG. 12 is a side view of an implant illustrating various bone on-growth structures, according to an embodiment of the disclosure.

FIG. 12 illustrates a side view of an implant 1200 having a superior end 1210, an inferior end 1220, a left side wall 1232, a right side wall 1234, and multiple bone on-growth structures 1250. Some of the bone on-growth structures 1250 have a root coupled to the left side wall 1232 of the implant 1200, and other bone on-growth structures 1250 have a root coupled to the right side wall 1234 of the implant 1200. In this example, each of the bone on-growth structures 1250 includes a root that is directly aligned opposite another root along the left and right side walls 1232, 1234 of the implant 1200. Moreover, in this example, none of the branches of the bone on-growth structures 1250 sufficiently extends toward an opposing end of the implant 1200, such that at least one branch contacts an opposing end of the implant 1200. Rather, each branch of the bone on-growth structures 1250 terminates within the interior space of the implant 1200.

Figure 13:
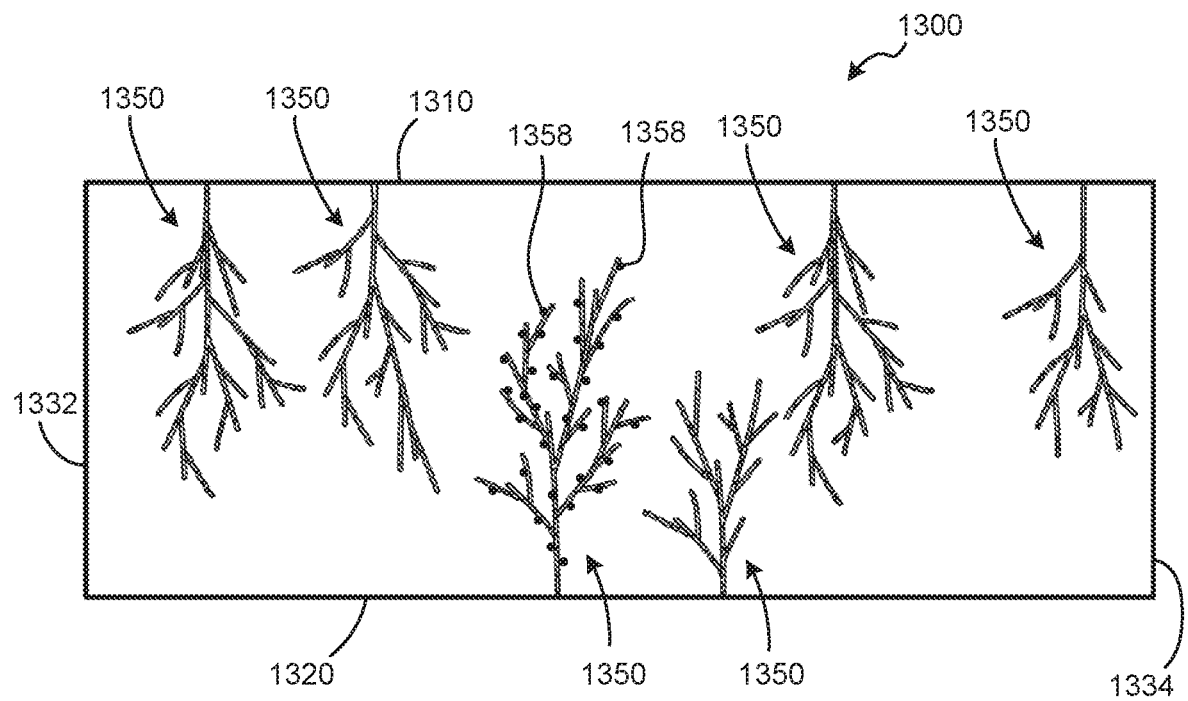
FIG. 13 is a side view of an implant illustrating various bone on-growth structures, according to an embodiment of the disclosure.

FIG. 13 illustrates a side view of an implant 1300 having a superior end 1310, an inferior end 1320, a left side wall 1332, a right side wall 1334, and multiple bone on-growth structures 1350. Some of the bone on-growth structures 1350 have a root coupled to the superior end 1310 of the implant 1300, and other bone on-growth structures 1350 have a root coupled to the inferior end 1320 of the implant 1300. In this example, none of the bone on-growth structures 1350 include a root that is directly aligned opposite another root along the superior and inferior ends 1310, 1320 of the implant 1300. Moreover, in this example, none of the branches of the bone on-growth structures 1350 sufficiently extends toward an opposing end of the implant 1300, such that at least one branch contacts an opposing end of the implant 1300. Rather, each branch of the bone on-growth structures 1350 terminates within the interior space of the implant 1300. Additionally, one or more of the bone on-growth structures 1350 may include a surface treatment 1358 to facilitate bone in-growth. The surface treatment 1358 may include, but is not limited to: a textured surface, a nano-textured surface, a biologic, a bioactive agent, hydroxyapatite, demineralized bone matrix ("DBM"), bone morphogenetic proteins ("BMP"), stem cells, and the like.

Figure 14:
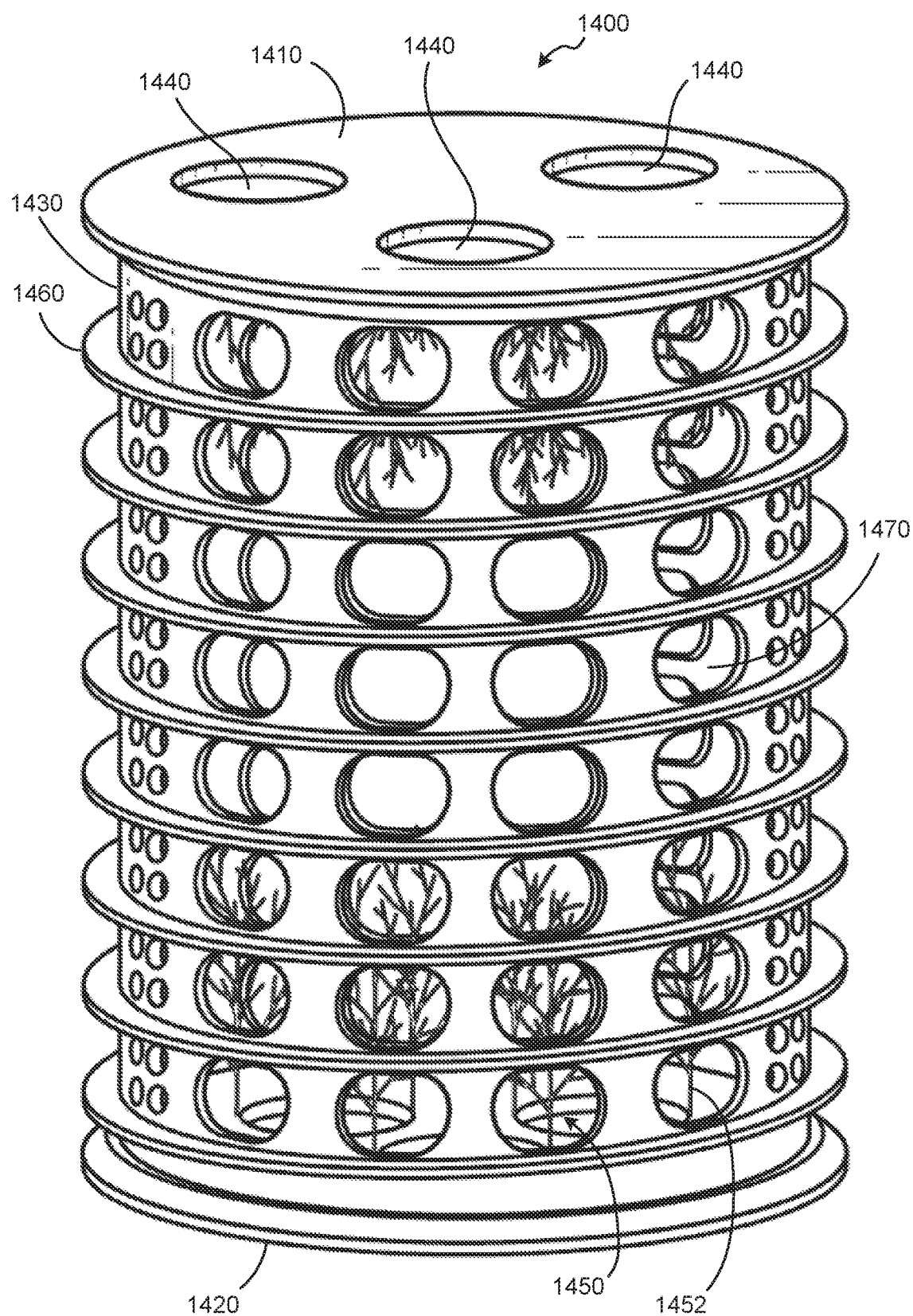
FIG. 14 is a top perspective view of an implant with various bone on-growth structures, according to an embodiment of the disclosure.

FIG. 14 illustrates an implant 1400 having a cylindrical shape, according to an embodiment of the disclosure. The implant 1400 shown in FIG. 14 includes a superior end 1410, an inferior end 1420, and a side wall 1430 intermediate the superior end 1410 and the inferior end 1420 of the implant 1400. The side wall 1430 may be coupled to both the superior end 1410 and the inferior end 1420 of the implant 1400, and may comprises a single, continuous wall that encompasses the entire implant 1400 intermediate the superior end 1410 and the inferior end 1420 of the implant 1400. An interior space of the implant 1400 may be defined by a combination of the superior end 1410, the inferior end 1420, and the side wall 1430 of the implant 1400, which together may enclose the interior space of the implant 1400.

The implant 1400 may include three channels 1440 which may be formed through opposing ends of the implant 1400 (e.g., through the superior and inferior ends 1410, 1420 of the implant 1400). The implant 1400 may also include additional channels 1470 which may be formed in the side wall 1430 of the implant 1400. The superior end 1410, the inferior end 1420, and/or the side wall 1430 of the implant 1400 may, in some embodiments, be formed of a solid material. In other embodiments, the superior end 1410, the inferior end 1420, and/or the side wall 1430 of the implant 1400 may be formed of a porous material.

The implant 1400 may also include a threaded structure 1460 that may wrap around the side wall 1430 of the implant 1400. The threaded structure 1460 may facilitate insertion of the implant 1400 within bone and/or between one or more bones. For example, the implant 1400 may be inserted between two adjacent vertebral bodies (not shown) by rotating the implant 1400 and engaging the threaded structure 1460 with the vertebral bodies to forcibly insert the implant 1400 between the vertebral bodies.

The implant 1400 may also include multiple bone on-growth structures 1450 disposed within the interior space of the implant 1400, as previously discussed. The roots 1452 of the bone on-growth structures 1450 may be coupled to an edge of the channels 1440 formed in the superior and inferior ends 1410, 1420 of the implant 1400 and the roots 1452 may extend into the interior space of the implant 1400 toward an opposing end of the implant 1400. Similar to previous examples discussed herein, each of the branches of the bone on-growth structures 1450 may terminate within the interior space of the implant 1400, such that they do not contact opposing ends of the implant 1400.

Figure 15:
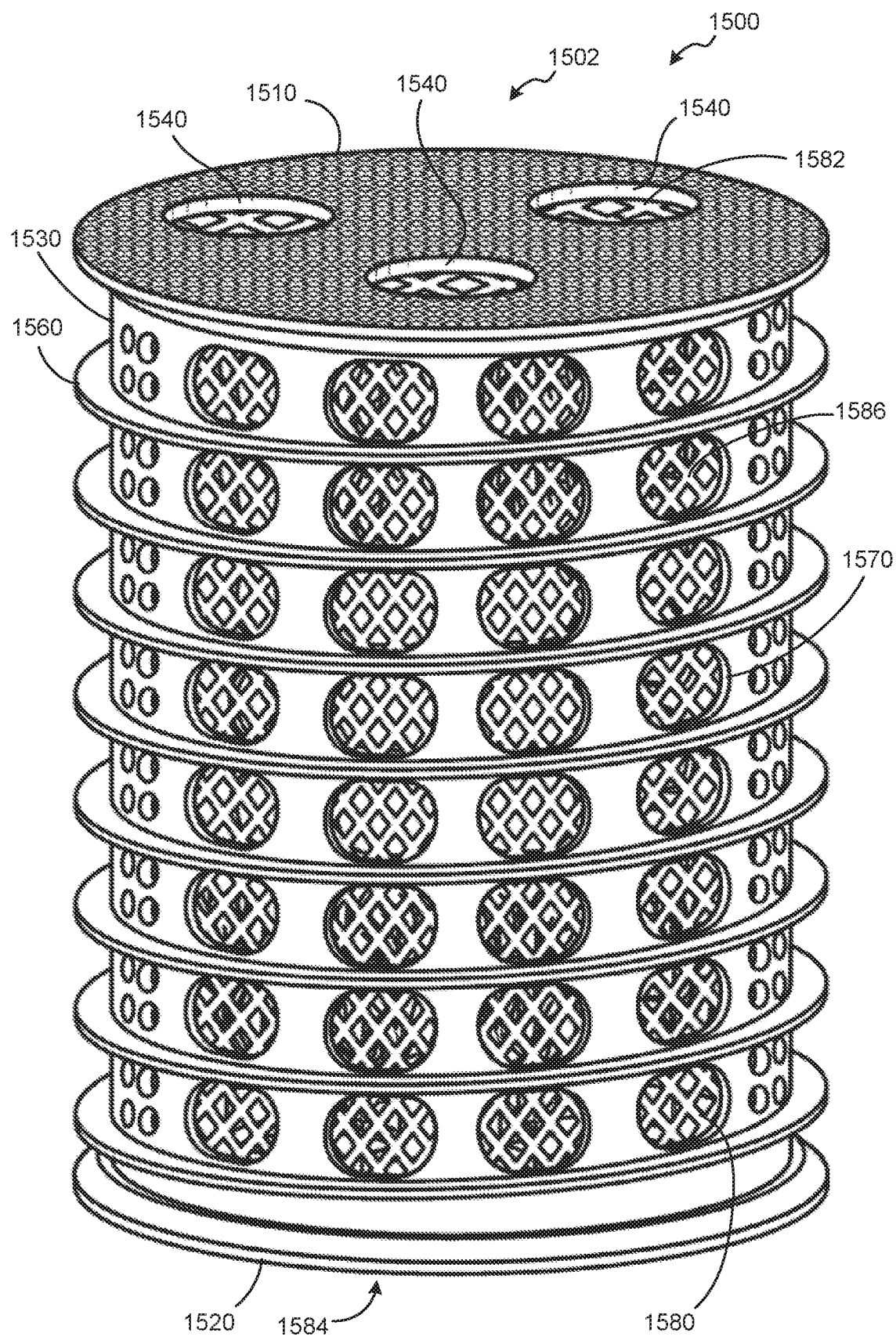
FIG. 15 is a top perspective view of an implant with an internal mesh insert including various bone on-growth structures, according to an embodiment of the disclosure.

FIG. 15 illustrates another implant 1500 having a cylindrical shape, according to an embodiment of the disclosure. The implant 1500 may include a fusion cage 1502 and a mesh insert 1580 that may be removably disposable within an interior space of the fusion cage 1502.

The fusion cage 1502 may include a fusion cage superior end 1510, a fusion cage inferior end 1520, and a fusion cage side wall 1530 intermediate the fusion cage superior end 1510 and the fusion cage inferior end 1520. At least one of the fusion cage superior end 1510 and the fusion cage inferior end 1520 may be removably couplable from the fusion cage side wall 1530. The fusion cage side wall 1530 may comprise a single, continuous wall that encompasses the entire fusion cage 1502 intermediate the fusion cage superior end 1510 and the fusion cage inferior end 1520. Thus, an interior space of the fusion cage 1502 may be defined by a combination of the fusion cage superior end 1510, the fusion cage inferior end 1520, and the fusion cage side wall 1530, which together may enclose the interior space of the fusion cage 1502.

The mesh insert 1580 may include a mesh insert superior end 1582, a mesh insert inferior end 1584, and a mesh insert side wall 1586 intermediate the mesh insert superior end 1582 and the mesh insert inferior end 1584. In at least one embodiment, the mesh insert 1580 may be formed via a 3D printing process. In another embodiment, the mesh insert 1580 may be formed via a chemical deposition process. The mesh insert side wall 1586 may comprise a single, continuous wall that encompasses the entire mesh insert 1580 intermediate the mesh insert superior end 1582 and the mesh insert inferior end 1584. Thus, an interior space of the mesh insert 1580 may be defined by a combination of the mesh insert superior end 1582, the mesh insert inferior end 1584, and the mesh insert side wall 1586, which together may enclose the interior space of the mesh insert 1580. The superior ends 1510, 1582, the inferior ends 1520, 1584, and/or the side walls 1530, 1586 of the fusion cage 1502 and/or the mesh insert 1580 may, in some embodiments, be formed of a solid material. In other embodiments, the superior ends 1510, 1582, the inferior ends 1520, 1584, and/or the side walls 1530, 1586 of the fusion cage 1502 and/or the mesh insert 1580 may be formed of a porous material. In still other embodiments, the fusion cage superior end 1510 and/or the fusion cage inferior end 1520 may be absent.

The fusion cage 1502 and/or the mesh insert 1580 may include one or more fusion cage channels (e.g., in this example there are three channels 1540) and/or one or more mesh insert channels (not shown), which may be formed through opposing ends of the fusion cage 1502 and/or the mesh insert 1580. The fusion cage 1502 and/or the mesh insert 1580 may also include additional channels 1570 which may be formed in the side walls 1530, 1586. In at least one embodiment, the one or more fusion cage channels 1540 may align with the one or more mesh insert channels (not shown), when the mesh insert 1580 is retained within the fusion cage 1502.

The fusion cage 1502 may also include a threaded structure 1560 that wraps around the fusion cage side wall 1530. The threaded structure 1560 may facilitate insertion of the fusion cage 1502 within bone (or between bones) by rotating the fusion cage 1502 to engage the threaded structure 1560 with one or more bones to forcibly insert the fusion cage 1502 within a bone, or between multiple bones.

The fusion cage 1502 may also include multiple bone on-growth structures disposed within the interior space of the mesh insert 1580, similar to other implants discussed above. For example, in at least one embodiment, a first root of a bone on-growth structure may be coupled to a first end of the mesh insert 1580, and a second root of a bone on-growth structure may be coupled to a second end of the mesh insert 1580 that is opposite the first end. However, it will be understood that the roots of such bone on-growth structures may be coupled to any surface, edge, or member of the mesh insert 1580 (e.g., a root may be coupled to an edge of one or more mesh insert 1580 channels) and the roots of such bone on-growth structures may extend into the interior space of the mesh insert 1580 toward an opposing end (or another end) of the mesh insert 1580. In at least one embodiment, each branch of the bone on-growth structures may terminate within the interior space of the mesh insert 1580, such that they do not contact an opposing ends of the mesh insert 1580. However, in other embodiments, at least one branch may contact an opposing end (or another end) of the mesh insert 1580.

It will be understood that FIGS. 14 and 15 merely illustrate two non-limiting example implants 1400, 1500 utilizing bone on-growth structures disclosed herein, and that any number of other different implant designs, configurations, and/or shapes may also utilize the bone on-growth structures disclosed herein. Moreover, it will be understood that FIGS. 14 and 15 are not necessarily drawn to scale, and other shapes for these implants 1400, 1500 are contemplated herein. For example, in some embodiments the implants 1400, 1500 may be shorter in the superior/inferior direction than in the medial/lateral and/or anterior posterior directions. It will also be understood that the implants 1400, 1500 may be inserted between two vertebral bodies with the longitudinal axis of the implants 1400, 1500 oriented along the superior/inferior direction, the medial/lateral direction, or the anterior/posterior direction, or any combination thereof.

Figure 16:
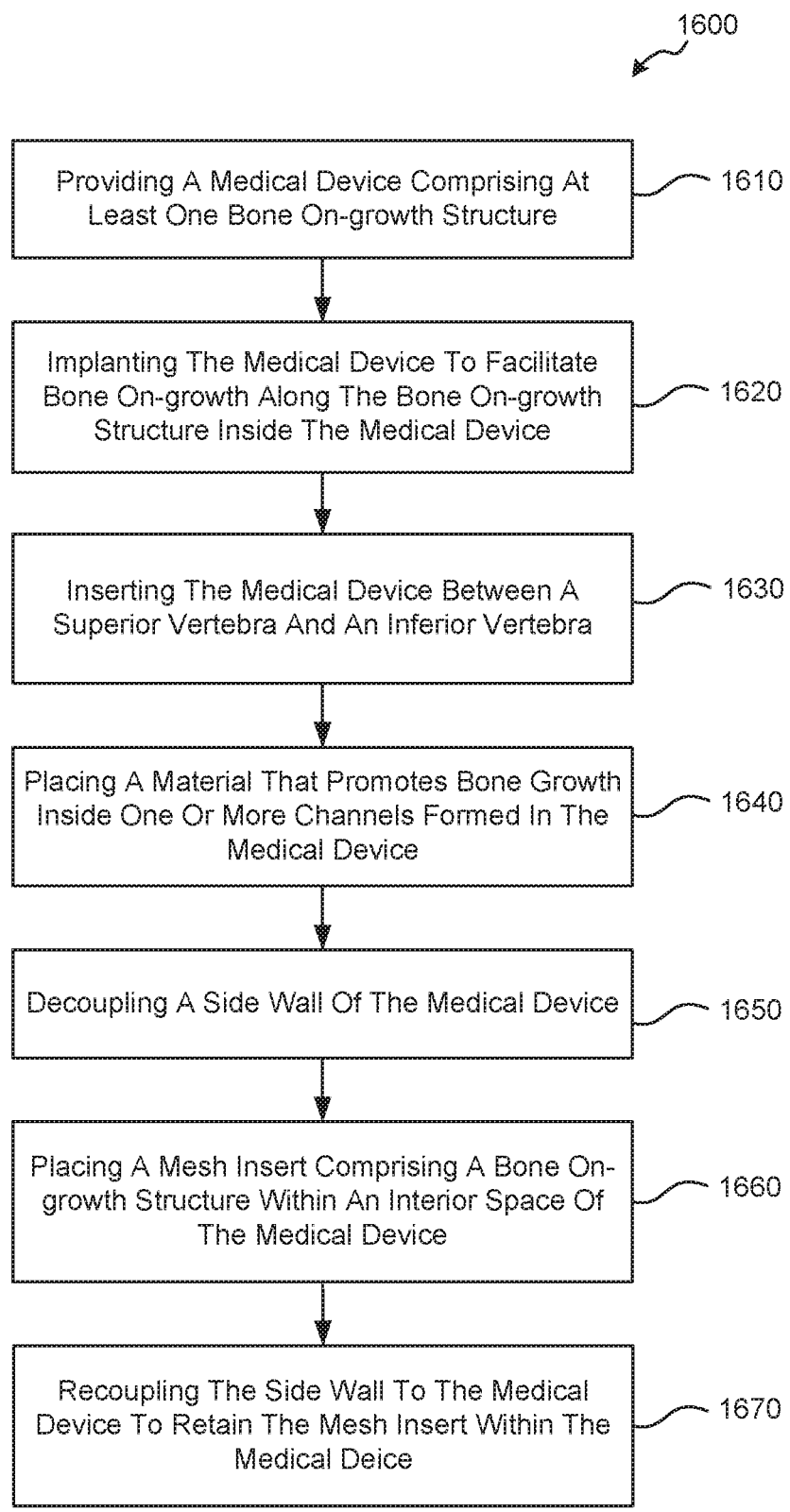
FIG. 16 is a flowchart of a method for implanting medical devices, according to embodiments of the present disclosure.

FIG. 16 illustrates a flowchart of a method 1600 by which a medical device of the present disclosure may be implanted within a patient.

The method 1600 may begin with a step 1610 in which a medical device comprising at least one bone on-growth structure may be provided. The medical device may be any medical device disclosed herein, or any medical device that may be envisioned by one of skill in the art in light of the teachings of the present disclosure.

Once such a medical device has been provided, the method 1600 may proceed to a step 1620 in which the medical device may be implanted inside a patient in order to facilitate bone on-growth along the at least one bone on-growth structure disposed within the medical device. The medical device may be implanted within bone, between one or more bones, and/or proximate bone in order to promote bone on-growth along the at least one bone on-growth structure disposed inside the medical device.

For example, step 1630 illustrates one example of a surgical procedure where the medical device may inserted between a superior vertebra and an inferior vertebra of a patient in order to fuse a vertebral joint of the patient by facilitating bone on-growth along the first bone on-growth structure within the medical device. However, it will be understood that the medical devices disclosed herein may be used in any number of different surgical procedures.

Alternatively, or in addition thereto, the method 1600 may include a step 1640 in which at least one material that promotes bone growth may be placed inside one or more channels formed in the medical device (and/or may be used to coat all or a portion of the medical device) in order to promote bone growth within the medical device along the bone on-growth structure, as previously discussed herein. For example, the at least one material may include, but is not limited to: a surface texturing, a nano-surface texturing, a biologic, a bioactive agent, hydroxyapatite, demineralized bone matrix ("DBM"), bone morphogenetic proteins ("BMP"), stem cells, and the like.

Alternatively, or in addition thereto, for at least some medical device embodiments disclosed herein, the method 1600 may additionally include steps 1650, 1660, and 1670. For example, in a step 1650, a side wall, a superior end, and/or an inferior end of the medical device (or fusion cage) may be decoupled from the medical device. In a step 1660, a mesh insert comprising at least one bone on-growth structure may then be placed within an interior space of the medical device (e.g., as previously described above with respect to FIG. 15). Once the mesh insert has been placed within the interior space of the medical device, the method 1600 may proceed to a step 1670 in which the side wall, the superior end, and/or the inferior end of the medical device may be recoupled to the medical device in order to retain the mesh insert within the medical device, and the method 1600 may end.

Any methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified, interchanged, omitted, or supplemented.

Figure 17:
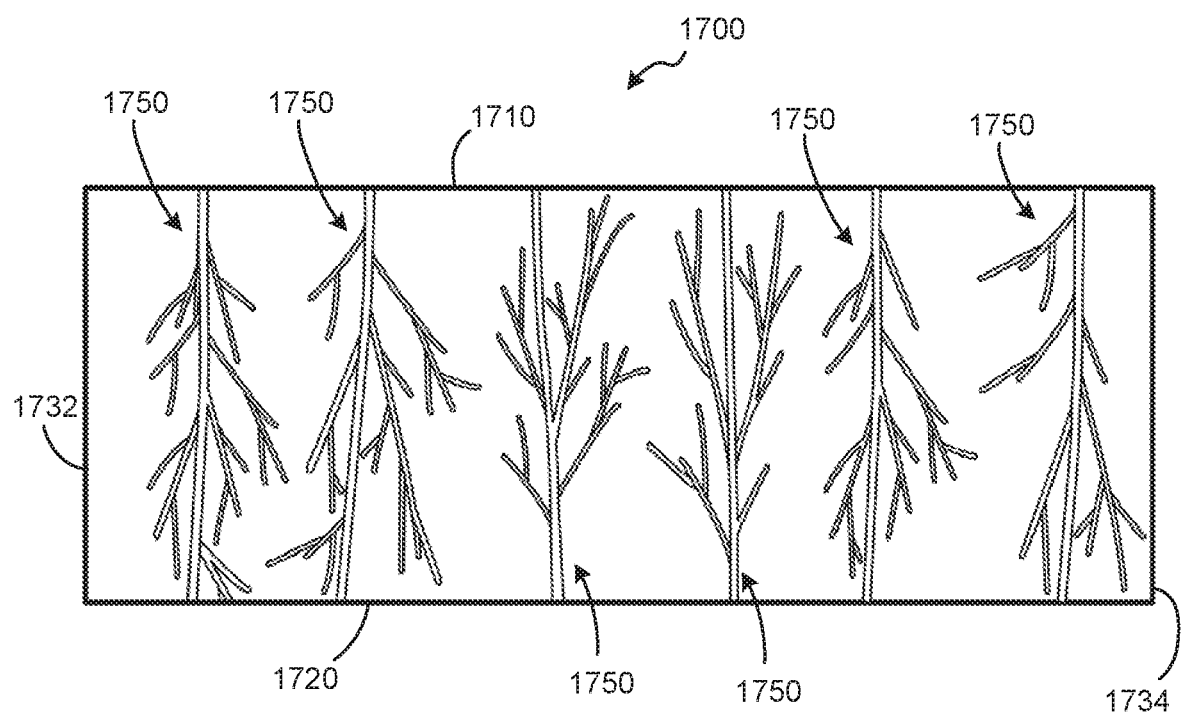
FIG. 17 is a side view of an implant illustrating various bone on-growth structures, according to an embodiment of the disclosure.

FIG. 17 illustrates a side view of an implant 1700 having a superior end 1710, an inferior end 1720, a left side wall 1732, a right side wall 1734, and multiple bone on-growth structures 1750, according to another embodiment of the disclosure. In this example, each bone on-growth structure 1750 includes a root that spans across the implant 1700 and couples to both of the superior and inferior ends 1710, 1720 of the implant 1700. In at least one embodiment, one or more of these roots may be larger in diameter than the branches which project from the root. Moreover, each of these larger central roots may be straight, substantially straight, angled, and/or curved. Additionally, it will be understood that these larger central roots may couple to any side wall, or other wall, of a given implant. In this manner, these larger central roots may provide additional strength for bone on-growth structures.

Figure 18:
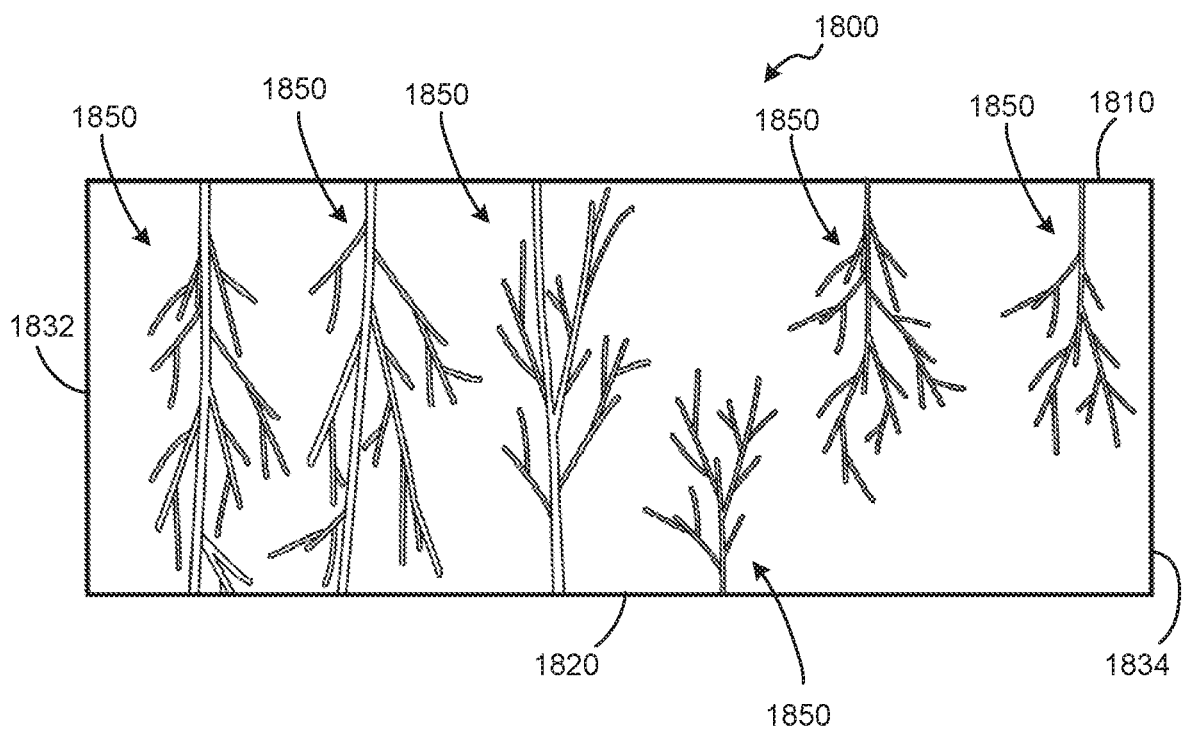
FIG. 18 is a side view of an implant illustrating various bone on-growth structures, according to an embodiment of the disclosure.

FIG. 18 illustrates a side view of an implant 1800 having a superior end 1810, an inferior end 1820, a left side wall 1832, a right side wall 1834, and multiple bone on-growth structures 1850, according to another embodiment of the disclosure. In this example, some of the bone on-growth structures 1850 may include a root that spans across the implant 1800 and couples to both of the superior and inferior ends 1810, 1820 of the implant 1800. However, other bone on-growth structures 1850 may include roots that do not span across the entire implant 1800. Likewise, any of these roots may be larger in diameter than the branches which project from the root. In this manner, different root configurations of any size, configuration, or orientation may be utilized within an implant.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Similarly, it will be appreciated that in the above description of embodiments, various features are sometimes grouped together in a single embodiment, figure, or description for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Only elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure herein without departing from the spirit and scope of the disclosure.

What is claimed is:

1. An implant comprising:
   a superior end;
   an inferior end displaced from the superior end along a longitudinal axis;
   at least one side wall intermediate and coupled to the superior end and the inferior end to define an interior space of the implant; and
   a first bone on-growth structure extending within the interior space of the implant, the first bone on-growth structure comprising:
      a first root coupled to one of:
         the superior end;
         the inferior end; and
         the at least one side wall of the implant;
      the first root extending into the interior space of the implant toward another one of:
         the superior end;
         the inferior end; and
         the at least one side wall of the implant; and
      a first plurality of branches coupled to the first root at a first plurality of junctions, the first plurality of branches projecting at a first plurality of different angles with respect to the first root, wherein each branch, of the first plurality of branches, extends nonperpendicular to the longitudinal axis and terminates within the interior space of the implant.

2. The implant of claim 1, wherein at least one branch of the first plurality of branches extends toward and contacts at least one of:
   the superior end;
   the inferior end; and
   the at least one side wall of the implant.

3. The implant of claim 1, wherein the first bone on-growth structure is formed via at least one of:
   a 3D printing process; and
   a chemical deposition process.
4. The implant of claim 1, wherein the first bone on-growth structure further comprises a textured surface to facilitate bone in-growth.
5. The implant of claim 1, further comprising:
   one or more channels formed in at least one of:
     the superior end;
     the inferior end; and
     the at least one side wall of the implant, the one or more channels oriented to pass through opposing ends of the implant;
   wherein the first root is coupled to an edge of the one or more channels and extends into the interior space of the implant toward another one of:
     the superior end;
     the inferior end; and
     the at least one side wall of the implant.
6. The implant of claim 1, further comprising:
   a second bone on-growth structure extending within the interior space of the implant, the second bone on-growth structure comprising:
     a second root coupled to one of:
       the superior end;
       the inferior end; and
       the at least one side wall of the implant;
     the second root extending into the interior space of the implant toward another one of:
       the superior end;
       the inferior end; and
       the at least one side wall of the implant; and
     a second plurality of branches coupled to the second root at a second plurality of junctions, the second plurality of branches projecting at a second plurality of different angles with respect to the second root,
     wherein the first root and the second root are each coupled to opposing ends of the implant.
7. An implant comprising:
   a fusion cage, the fusion cage comprising:
     a fusion cage superior end;
     a fusion cage inferior end displaced from the fusion cage superior end along a longitudinal axis; and
     at least one fusion cage side wall intermediate the fusion cage superior end and the fusion cage inferior end, defining an interior space of the fusion cage,
     wherein at least one of the fusion cage superior end and the fusion cage inferior end are removably couplable from the at least one fusion cage side wall; and
   a mesh insert removably disposable within the interior space of the fusion cage, the mesh insert comprising:
     a mesh insert superior end;
     a mesh insert inferior end;
     at least one mesh insert side wall intermediate, and coupled to, the mesh insert superior end and the mesh insert inferior end to define an interior space of the mesh insert; and
     a first bone on-growth structure extending within the interior space of the mesh insert, the first bone on-growth structure comprising:
       a first root coupled to one of:
         the mesh insert superior end;
         the mesh insert inferior end; and
         the at least one mesh insert side wall;
       the first root extending into the interior space of the mesh insert toward another one of:
         the mesh insert superior end;
         the mesh insert inferior end; and
         the at least one mesh insert side wall; and
       a first plurality of branches coupled to the first root at a first plurality of junctions, the first plurality of branches projecting at a first plurality of different angles with respect to the first root, wherein each branch, of the first plurality of branches, extends nonperpendicular to the longitudinal axis and terminates within the interior space of the mesh insert.
8. The implant of claim 7, wherein at least one branch of the first plurality of branches extends toward and contacts at least one of:
   the mesh insert superior end;
   the mesh insert inferior end; and
   the at least one mesh insert side wall.
9. The implant of claim 7, wherein the first bone on-growth structure is formed via at least one of:
   a 3D printing process; and
   a chemical deposition process.
10. The implant of claim 7, wherein the first bone on-growth structure further comprises a textured surface to facilitate bone in-growth.
11. The implant of claim 7, further comprising:
    one or more fusion cage channels formed in at least one of:
      the fusion cage superior end;
      the fusion cage inferior end; and
      the at least one fusion cage side wall, the one or more fusion cage channels oriented to pass through opposing ends of the fusion cage; and
    one or more mesh insert channels formed in at least one of:
      the mesh insert superior end;
      the mesh insert inferior end; and
      the at least one mesh insert side wall, the one or more mesh insert channels oriented to pass through opposing ends of the mesh insert,
    wherein the first root is coupled to an edge of the one or more mesh insert channels and extends into the interior space of the mesh insert toward another one of:
      the mesh insert superior end;
      the mesh insert inferior end; and
      the at least one mesh insert side wall;
    and wherein the one or more fusion cage channels align with the one or more mesh insert channels when the mesh insert is retained within the fusion cage.
12. The implant of claim 7, further comprising:
    a second bone on-growth structure extending within the interior space of the mesh insert, the second bone on-growth structure comprising:
      a second root coupled to one of:
        the mesh insert superior end;
        the mesh insert inferior end; and
        the at least one mesh insert side wall;
      the second root extending into the interior space of the mesh insert toward another one of:
        the mesh insert superior end;
        the mesh insert inferior end; and
        the at least one mesh insert side wall; and
      a second plurality of branches coupled to the second root at a second plurality of junctions, the second plurality of branches projecting at a second plurality of different angles with respect to the second root, wherein the first root and the second root are each coupled to opposing ends of the mesh insert.

13. A method of facilitating bone on-growth within an implantable medical device, the method comprising:
   providing a medical device, the medical device comprising:
      a superior end;
      an inferior end;
      at least one side wall intermediate and coupled to the superior end and the inferior end to define an interior space of the medical device; and
      a first bone on-growth structure extending within the interior space of the medical device, the first bone on-growth structure comprising:
         a first root coupled to one of:
            the superior end;
            the inferior end; and
            the at least one side wall of the medical device;
         the first root extending into the interior space of the medical device toward another one of:
            the superior end;
            the inferior end; and
            the at least one side wall of the medical device; and
         a first plurality of branches coupled to the first root at a first plurality of junctions, each of which has a random number of the branches, the first plurality of branches projecting at a first plurality of different angles with respect to the first root, wherein each branch, of the first plurality of branches, terminates within the interior space of the medical device; and
   implanting the medical device within a patient to facilitate bone on-growth along the first bone on-growth structure within the medical device.

14. The method of claim 13, wherein implanting the medical device within a patient further comprises:
   inserting the medical device between a superior vertebra and an inferior vertebra to fuse a vertebral joint of the patient by facilitating bone on-growth along the first bone on-growth structure within the medical device.

15. The method of claim 13, wherein:
   the medical device further comprises:
      one or more channels formed in at least one of:
         the superior end;
         the inferior end; and
         the at least one side wall of the medical device, the one or more channels oriented to pass through opposing ends of the medical device; and
   the method further comprises:
      placing at least one material that promotes bone growth inside the one or more channels formed in the medical device in order to promote bone growth within the medical device along the first bone on-growth structure.

16. The method of claim 13, wherein:
   the medical device further comprises:
      a fusion cage, the fusion cage comprising:
         a fusion cage superior end;
         a fusion cage inferior end; and
         at least one fusion cage side wall intermediate the fusion cage superior end and the fusion cage inferior end, defining an interior space of the fusion cage,
         wherein at least one of the fusion cage superior end and the fusion cage inferior end are removably couplable from the at least one fusion cage side wall; and
      a mesh insert removably disposable within the interior space of the fusion cage, the mesh insert comprising:
         a mesh insert superior end;
         a mesh insert inferior end; and
         at least one mesh insert side wall intermediate, and coupled to, the mesh insert superior end and the mesh insert inferior end to define an interior space of the mesh insert;
         wherein the first bone on-growth structure extends within the interior space of the mesh insert with the first root coupled to one of:
            the mesh insert superior end;
            the mesh insert inferior end; and
            the at least one mesh insert side wall, and wherein the first root extends into the interior space of the mesh insert toward another one of:
            the mesh insert superior end;
            the mesh insert inferior end; and
            the at least one mesh insert side wall; and
   the method further comprises:
      decoupling at least one of the fusion cage superior end and the fusion cage inferior end from the at least one fusion cage side wall;
      placing the mesh insert within the interior space of the fusion cage; and
      recoupling the at least one of the fusion cage superior end and the fusion cage inferior end to the at least one fusion cage side wall, such that the mesh insert is retained within the interior space of the fusion cage.

17. The method of claim 13, wherein at least one branch of the first plurality of branches extends toward and contacts at least one of:
   the superior end;
   the inferior end; and
   the at least one side wall of the medical device.

* * * * *